United States Patent
Lubock et al.

(10) Patent No.: US 10,478,161 B2
(45) Date of Patent: Nov. 19, 2019

(54) TISSUE CUTTING MEMBER FOR A BIOPSY DEVICE

(71) Applicant: SenoRx, Inc., Tempe, AZ (US)

(72) Inventors: Paul Lubock, Monarch Beach, CA (US); Frank R. Louw, Carlsbad, CA (US); Richard L. Quick, Mission Viejo, CA (US)

(73) Assignee: SenoRx, Inc., Franklin Lakes, NJ (US)

( * ) Notice: Subject to any disclaimer, the term of this patent is extended or adjusted under 35 U.S.C. 154(b) by 273 days.

(21) Appl. No.: 15/692,242

(22) Filed: Aug. 31, 2017

(65) Prior Publication Data

US 2017/0360417 A1 Dec. 21, 2017

Related U.S. Application Data

(60) Division of application No. 14/755,244, filed on Jun. 30, 2015, now Pat. No. 9,750,487, which is a
(Continued)

(51) Int. Cl.
*A61B 5/00* (2006.01)
*A61B 10/02* (2006.01)
(Continued)

(52) U.S. Cl.
CPC ...... *A61B 10/0275* (2013.01); *A61B 10/0283* (2013.01); *A61B 17/320016* (2013.01); *A61B 17/3417* (2013.01)

(58) Field of Classification Search
CPC ............ A61B 10/0275; A61B 10/0283; A61B 17/3417; A61B 17/320016
See application file for complete search history.

(56) References Cited

U.S. PATENT DOCUMENTS

| 2,032,860 A | 3/1936 | Wappler et al. |
| 3,341,417 A | 9/1967 | Sinaiko |

(Continued)

FOREIGN PATENT DOCUMENTS

| DE | 1225813 B | 9/1966 |
| DE | 19528440 A1 | 2/1997 |

(Continued)

OTHER PUBLICATIONS

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.
(Continued)

*Primary Examiner* — Max F Hindenburg

(57) ABSTRACT

A method for forming a tissue cutting member includes: providing a single longitudinally oriented opening in a side wall in a flared distal section of a distal tubular portion which radially opens to a lumen of the distal tubular portion, the single longitudinally oriented opening having an open distal end and extending from a closed proximal end to the open distal end; and providing a relief opening at the closed proximal end of the single longitudinally oriented opening, the relief opening having a transverse dimension larger than a transverse dimension of the single longitudinally oriented opening adjacent the relief opening, the single longitudinally oriented opening diverging from the closed proximal end to intersect a trailing cutting edge of a beveled front face of the inclined distal tip of the distal tubular portion and facilitating formation of the outwardly flared distal tubular portion.

19 Claims, 19 Drawing Sheets

Related U.S. Application Data continuation of application No. 11/438,955, filed on May 22, 2006, now Pat. No. 9,095,325.

(60) Provisional application No. 60/683,584, filed on May 23, 2005.

(51) Int. Cl.
    *A61B 17/32*      (2006.01)
    *A61B 17/34*      (2006.01)

(56) References Cited

U.S. PATENT DOCUMENTS

| | | |
|---|---|---|
| 3,805,791 A | 4/1974 | Seuberth et al. |
| 3,818,894 A | 6/1974 | Wichterle et al. |
| 3,823,212 A | 7/1974 | Chvapil |
| 3,844,272 A | 10/1974 | Banko |
| 3,847,153 A | 11/1974 | Weissman |
| 3,910,279 A | 10/1975 | Okada et al. |
| 3,945,375 A | 3/1976 | Banko |
| 3,955,578 A | 5/1976 | Chamness et al. |
| 4,007,732 A | 2/1977 | Kvavle et al. |
| 4,172,449 A | 10/1979 | Leroy et al. |
| 4,197,846 A | 4/1980 | Bucalo |
| 4,202,338 A | 5/1980 | Bitrolf |
| 4,243,048 A | 1/1981 | Griffin |
| 4,276,885 A | 7/1981 | Tickner et al. |
| 4,294,241 A | 10/1981 | Miyata |
| 4,294,254 A | 10/1981 | Chamness |
| 4,311,143 A | 1/1982 | Komiya |
| 4,331,654 A | 5/1982 | Morris |
| 4,362,160 A | 12/1982 | Hiltebrandt |
| 4,418,692 A | 12/1983 | Guay |
| 4,503,855 A | 3/1985 | Maslanka |
| 4,545,367 A | 10/1985 | Tucci |
| 4,565,200 A | 1/1986 | Cosman |
| 4,576,162 A | 3/1986 | Mccorkle |
| 4,638,802 A | 1/1987 | Okada |
| 4,643,187 A | 2/1987 | Okada |
| 4,647,480 A | 3/1987 | Ahmed |
| 4,682,606 A | 7/1987 | DeCaprio |
| 4,693,237 A | 9/1987 | Hoffman et al. |
| 4,718,419 A | 1/1988 | Okada |
| 4,724,836 A | 2/1988 | Okada |
| 4,813,062 A | 3/1989 | Gilpatrick |
| 4,819,635 A | 4/1989 | Shapiro |
| 4,847,049 A | 7/1989 | Yamamoto |
| 4,863,470 A | 9/1989 | Carter |
| 4,909,250 A | 3/1990 | Smith |
| 4,926,858 A | 5/1990 | Gifford, III et al. |
| 5,007,908 A | 4/1991 | Rydell |
| 5,024,617 A | 6/1991 | Karpiel |
| 5,035,696 A | 7/1991 | Rydell |
| 5,041,124 A | 8/1991 | Kensey |
| 5,047,027 A | 9/1991 | Rydell |
| 5,059,204 A | 10/1991 | Lawson et al. |
| 5,064,424 A | 11/1991 | Bitrolf |
| 5,066,295 A | 11/1991 | Kozak et al. |
| 5,078,716 A | 1/1992 | Doll |
| 5,080,660 A | 1/1992 | Buelna |
| 5,085,659 A | 2/1992 | Rydell |
| 5,106,364 A | 4/1992 | Hayafuji et al. |
| RE33,925 E | 5/1992 | Bales et al. |
| 5,111,828 A | 5/1992 | Komberg et al. |
| 5,133,359 A | 7/1992 | Kedem |
| 5,133,360 A | 7/1992 | Spears |
| RE34,056 E | 9/1992 | Lindgren et al. |
| 5,147,307 A | 9/1992 | Gluck |
| 5,158,561 A | 10/1992 | Rydell et al. |
| 5,163,938 A | 11/1992 | Kambara et al. |
| 5,196,007 A | 3/1993 | Ellman et al. |
| 5,201,732 A | 4/1993 | Parins et al. |
| 5,201,741 A | 4/1993 | Dulebohn |
| 5,207,686 A | 5/1993 | Dolgin |
| 5,217,458 A | 6/1993 | Parins |
| 5,224,488 A | 7/1993 | Neuffer |
| 5,236,410 A | 8/1993 | Granov et al. |
| 5,258,006 A | 11/1993 | Rydell et al. |
| 5,281,218 A | 1/1994 | Imran |
| 5,281,408 A | 1/1994 | Unger |
| 5,282,781 A | 2/1994 | Liprie |
| 5,312,400 A | 5/1994 | Bales et al. |
| 5,318,564 A | 6/1994 | Eggers |
| 5,320,613 A | 6/1994 | Houge et al. |
| 5,323,768 A | 6/1994 | Saito et al. |
| 5,324,288 A | 6/1994 | Billings et al. |
| 5,330,471 A | 7/1994 | Eggers |
| 5,334,381 A | 8/1994 | Unger |
| 5,335,671 A | 8/1994 | Clement |
| 5,344,381 A | 9/1994 | Cabrera y Lopez Caram |
| 5,344,420 A | 9/1994 | Hilal et al. |
| 5,366,468 A | 11/1994 | Fucci et al. |
| 5,368,030 A | 11/1994 | Zinreich et al. |
| 5,374,188 A | 12/1994 | Frank et al. |
| 5,376,094 A | 12/1994 | Kline |
| 5,380,321 A | 1/1995 | Yoon |
| 5,395,312 A | 3/1995 | Desai |
| 5,395,319 A | 3/1995 | Hirsch et al. |
| 5,401,272 A | 3/1995 | Perkins |
| 5,415,656 A | 5/1995 | Tihon et al. |
| 5,417,687 A | 5/1995 | Nardella et al. |
| 5,417,697 A | 5/1995 | Wilk et al. |
| 5,422,730 A | 6/1995 | Barlow et al. |
| 5,423,809 A | 6/1995 | Klcek |
| 5,423,814 A | 6/1995 | Zhu et al. |
| 5,431,649 A | 7/1995 | Mulier et al. |
| 5,433,204 A | 7/1995 | Olson |
| 5,437,665 A | 8/1995 | Munro |
| 5,441,498 A | 8/1995 | Perkins |
| 5,441,503 A | 8/1995 | Considine et al. |
| 5,462,553 A | 10/1995 | Dolgin |
| 5,470,308 A | 11/1995 | Edwards et al. |
| 5,477,862 A | 12/1995 | Haaga |
| 5,484,436 A | 1/1996 | Eggers et al. |
| 5,487,385 A | 1/1996 | Avitall |
| 5,488,958 A | 2/1996 | Topel et al. |
| 5,494,030 A | 2/1996 | Swartz et al. |
| 5,501,654 A | 3/1996 | Failla et al. |
| 5,507,743 A | 4/1996 | Edwards et al. |
| 5,510,070 A | 4/1996 | Krause et al. |
| 5,526,822 A | 6/1996 | Burbank et al. |
| 5,527,331 A | 6/1996 | Kresch et al. |
| 5,536,267 A | 7/1996 | Edwards et al. |
| 5,538,010 A | 7/1996 | Darr et al. |
| 5,542,948 A | 8/1996 | Weaver et al. |
| 5,549,560 A | 8/1996 | Van De Wijdeven |
| 5,578,030 A | 11/1996 | Levin |
| 5,595,185 A | 1/1997 | Erlich |
| 5,599,347 A | 2/1997 | Hart et al. |
| 5,607,389 A | 3/1997 | Edwards et al. |
| 5,611,803 A | 3/1997 | Heaven et al. |
| 5,636,255 A | 6/1997 | Ellis |
| 5,643,282 A | 7/1997 | Kieturakis |
| 5,646,146 A | 7/1997 | Faarup et al. |
| 5,649,547 A | 7/1997 | Ritchart et al. |
| 5,653,718 A | 8/1997 | Yoon |
| 5,665,085 A | 9/1997 | Nardella |
| 5,672,174 A | 9/1997 | Gough et al. |
| 5,674,184 A | 10/1997 | Hassler, Jr. |
| 5,676,663 A | 10/1997 | Kim |
| 5,676,925 A | 10/1997 | Klaveness et al. |
| 5,683,384 A | 11/1997 | Gough et al. |
| 5,687,739 A | 11/1997 | Mcpherson et al. |
| 5,688,490 A | 11/1997 | Tournier et al. |
| 5,715,825 A | 2/1998 | Crowley |
| 5,720,763 A | 2/1998 | Tovey |
| 5,741,225 A | 4/1998 | Lax et al. |
| 5,749,626 A | 5/1998 | Yoshida |
| 5,755,724 A | 5/1998 | Yoon |
| 5,766,169 A | 6/1998 | Fritzsch et al. |
| 5,769,086 A | 6/1998 | Ritchart et al. |
| 5,772,660 A | 6/1998 | Young et al. |
| 5,775,333 A | 7/1998 | Burbank et al. |
| 5,782,764 A | 7/1998 | Werne |

(56) References Cited

U.S. PATENT DOCUMENTS

| | | |
|---|---|---|
| 5,782,775 A | 7/1998 | Milliman et al. |
| 5,782,827 A | 7/1998 | Gough et al. |
| 5,794,626 A | 8/1998 | Kieturakis |
| 5,797,907 A | 8/1998 | Clement |
| 5,800,378 A | 9/1998 | Edwards et al. |
| 5,810,806 A | 9/1998 | Ritchart et al. |
| 5,814,044 A | 9/1998 | Hooven |
| 5,846,513 A | 12/1998 | Carroll et al. |
| 5,848,978 A | 12/1998 | Cecchi |
| 5,853,366 A | 12/1998 | Dowlatshahi |
| 5,857,981 A | 1/1999 | Bucalo et al. |
| 5,857,982 A | 1/1999 | Milliman et al. |
| 5,876,340 A | 3/1999 | Tu et al. |
| 5,882,316 A | 3/1999 | Chu et al. |
| 5,902,272 A | 5/1999 | Eggers et al. |
| 5,913,857 A | 6/1999 | Ritchart et al. |
| 5,925,044 A | 7/1999 | Hofmann et al. |
| 5,928,164 A | 7/1999 | Burbank et al. |
| 5,938,587 A | 8/1999 | Taylor et al. |
| 5,938,635 A | 8/1999 | Kuhle |
| 5,941,893 A | 8/1999 | Saadat |
| 5,947,964 A | 9/1999 | Eggers et al. |
| 5,954,670 A | 9/1999 | Baker |
| 5,964,716 A | 10/1999 | Gregoire et al. |
| 5,972,002 A | 10/1999 | Bark et al. |
| 5,980,469 A | 11/1999 | Burbank et al. |
| 5,984,919 A | 11/1999 | Hilal et al. |
| 5,997,560 A | 12/1999 | Miller |
| 6,004,269 A | 12/1999 | Crowley et al. |
| 6,024,751 A | 2/2000 | Lovato et al. |
| 6,036,681 A | 3/2000 | Hooven |
| 6,050,955 A | 4/2000 | Bryan et al. |
| 6,050,992 A | 4/2000 | Nichols |
| 6,056,700 A | 5/2000 | Burney et al. |
| 6,059,782 A | 5/2000 | Novak et al. |
| 6,063,082 A | 5/2000 | Devore et al. |
| 6,071,280 A | 6/2000 | Edwards et al. |
| 6,120,462 A | 9/2000 | Hibner et al. |
| 6,142,955 A | 11/2000 | Farascioni et al. |
| 6,161,034 A | 12/2000 | Burbank et al. |
| 6,203,524 B1 | 3/2001 | Burney et al. |
| 6,234,177 B1 | 5/2001 | Barsch |
| 6,254,601 B1 | 7/2001 | Burbank et al. |
| 6,258,111 B1 | 7/2001 | Ross et al. |
| 6,261,241 B1 | 7/2001 | Burbank et al. |
| 6,277,083 B1 | 8/2001 | Eggers et al. |
| 6,312,429 B1 | 11/2001 | Burbank et al. |
| 6,331,166 B1 | 12/2001 | Burbank et al. |
| 6,344,026 B1 | 2/2002 | Burbank et al. |
| 6,419,684 B1 | 7/2002 | Heisler et al. |
| 6,514,215 B1 | 2/2003 | Ouchi |
| 6,514,248 B1 | 2/2003 | Eggers et al. |
| 6,540,695 B1 | 4/2003 | Burbank et al. |
| 6,679,851 B2 | 1/2004 | Burbank et al. |
| 6,689,145 B2 | 2/2004 | Lee et al. |
| 6,758,824 B1 | 7/2004 | Miller et al. |
| 7,189,206 B2 | 3/2007 | Quick et al. |
| 7,226,424 B2 | 6/2007 | Ritchart et al. |
| 8,641,640 B2 | 2/2014 | Lubock et al. |
| 9,095,325 B2* | 8/2015 | Lubock ............ A61B 10/0275 |
| 9,750,487 B2* | 9/2017 | Lubock ............ A61B 10/0275 |
| 2001/0001811 A1 | 5/2001 | Burney et al. |
| 2001/0002250 A1 | 5/2001 | Burbank et al. |
| 2002/0016555 A1 | 2/2002 | Ritchart et al. |
| 2003/0004407 A1 | 1/2003 | Carroll et al. |
| 2003/0229293 A1 | 12/2003 | Hibner et al. |
| 2004/0019299 A1 | 1/2004 | Ritchart et al. |
| 2004/0167428 A1 | 8/2004 | Quick et al. |
| 2005/0159730 A1 | 7/2005 | Kathrani et al. |

FOREIGN PATENT DOCUMENTS

| | | |
|---|---|---|
| EP | 0146699 A1 | 7/1985 |
| EP | 0255123 A2 | 2/1988 |
| EP | 0292936 A2 | 11/1988 |
| EP | 0472368 A2 | 2/1992 |
| EP | 0481685 A1 | 4/1992 |
| EP | 0509670 A2 | 10/1992 |
| EP | 0601709 A2 | 6/1994 |
| EP | 0769281 A2 | 4/1997 |
| EP | 0858774 A2 | 8/1998 |
| EP | 0919190 A2 | 6/1999 |
| EP | 0966925 A1 | 12/1999 |
| EP | 0970658 A1 | 1/2000 |
| GB | 2311468 A | 10/1997 |
| WO | 9313718 A1 | 7/1993 |
| WO | 9314712 A1 | 8/1993 |
| WO | 9502370 A2 | 1/1995 |
| WO | 9502371 A2 | 1/1995 |
| WO | 9503843 A1 | 2/1995 |
| WO | 9608208 A1 | 3/1996 |
| WO | 9729702 A1 | 8/1997 |
| WO | 9806346 A1 | 2/1998 |
| WO | 9808441 A1 | 3/1998 |
| WO | 9843531 A1 | 10/1998 |
| WO | 9930764 A1 | 6/1999 |
| WO | 9944506 A1 | 9/1999 |
| WO | 0012009 A2 | 3/2000 |
| WO | 0016697 A2 | 3/2000 |
| WO | 0030531 A1 | 6/2000 |
| WO | 0149184 A2 | 7/2001 |
| WO | 0205717 A1 | 1/2002 |
| WO | 0222023 A1 | 3/2002 |
| WO | 03034915 A1 | 5/2003 |
| WO | 2005063126 A2 | 7/2005 |

OTHER PUBLICATIONS

Burbank, F., M.D., Stereotactic Breast Biopsy: Its History, Its Present, and Its Future, The American Surgeon, Feb. 1996, vol. 62, pp. 128-150.

Fucci, V., et al., "Large Bowel Transit Times Using Radioopaque Markers in Normal Cats", J. of Am. Animal Hospital Assn., Nov.-Dec. 1995 31 (6) 473-477.

Lorenzen, T. et al., The Loop Electrode: a New Device for US-guided Interstitial Tissue Ablation Using Radio frequency Electrosurgery—An Animal Study, 1996 Blackwell Science Ltd. Min Invas Ther & Allied Technol, pp. 5.511-5.516.

Micklos, Timothy J., Percutaneous Biopsy Techniques, Manual of Oncologic Therapeutics (1989/1990) pp. 39-42.

Schindlebeck, N. E., et al., "Measurement of Colon Transit Time", J. of Gastroenterology, No. 28, pp. 399-404, 1990.

Whitman, et al., Coaxial Core Needle Biopsy Under Mammographic Guidance: Indications and Applications, AJR:171, Jul. 1998, pp. 67-70.

International Search report in PCT/US2006/019959 dated Oct. 10, 2006.

Written Opinion of the International Searching Authority in PCT/US2006/019959 dated Oct. 10, 2006.

* cited by examiner

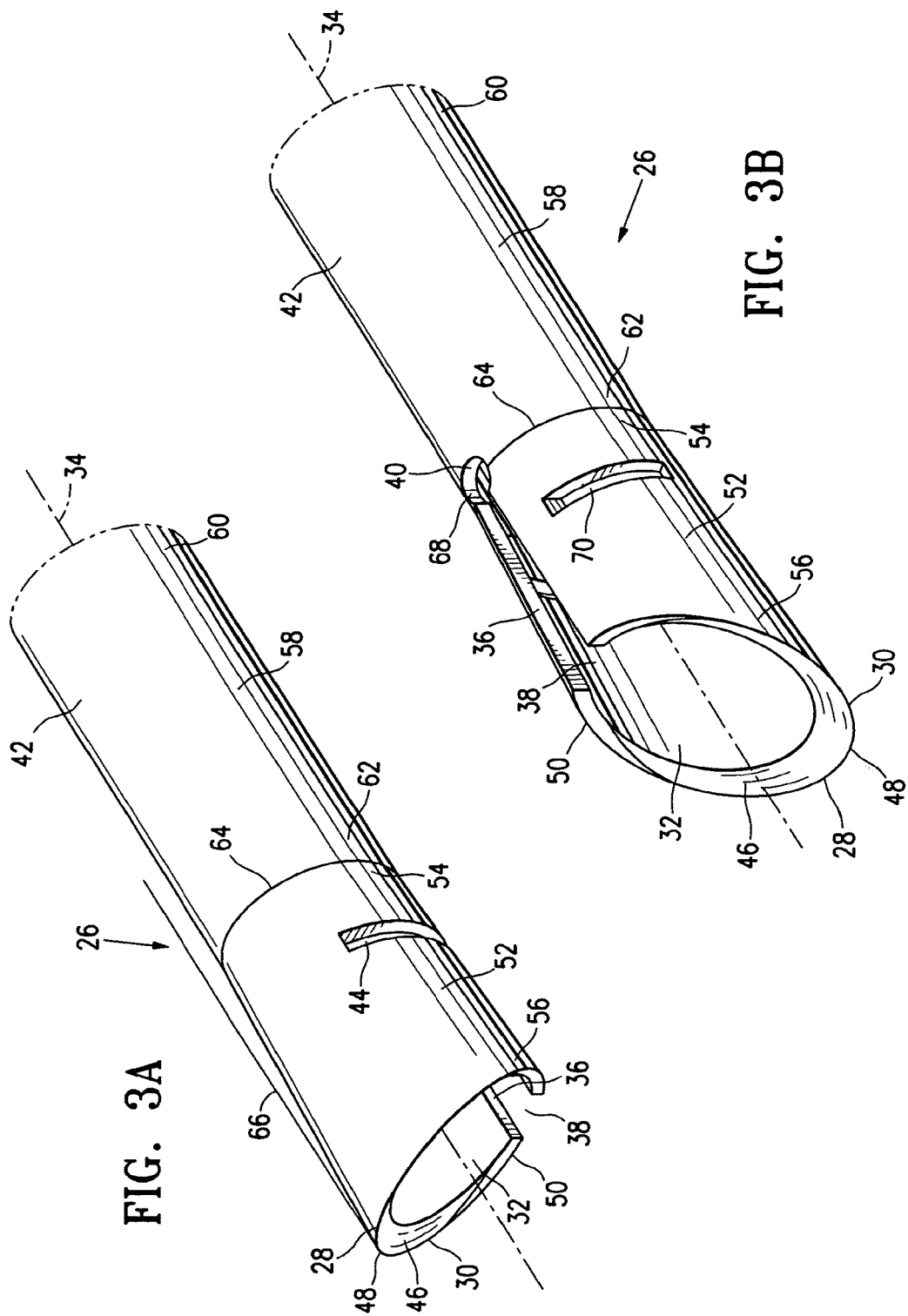

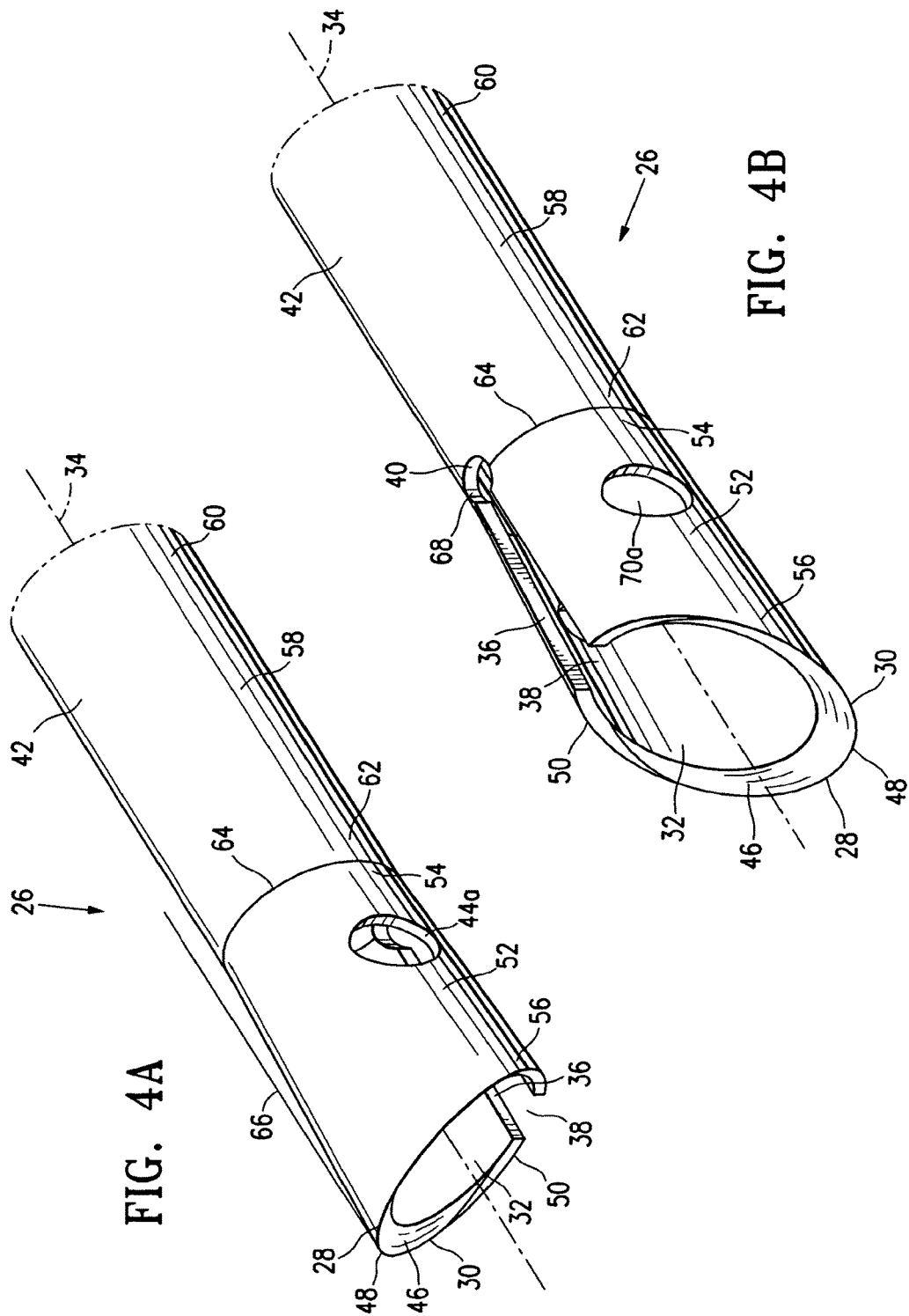

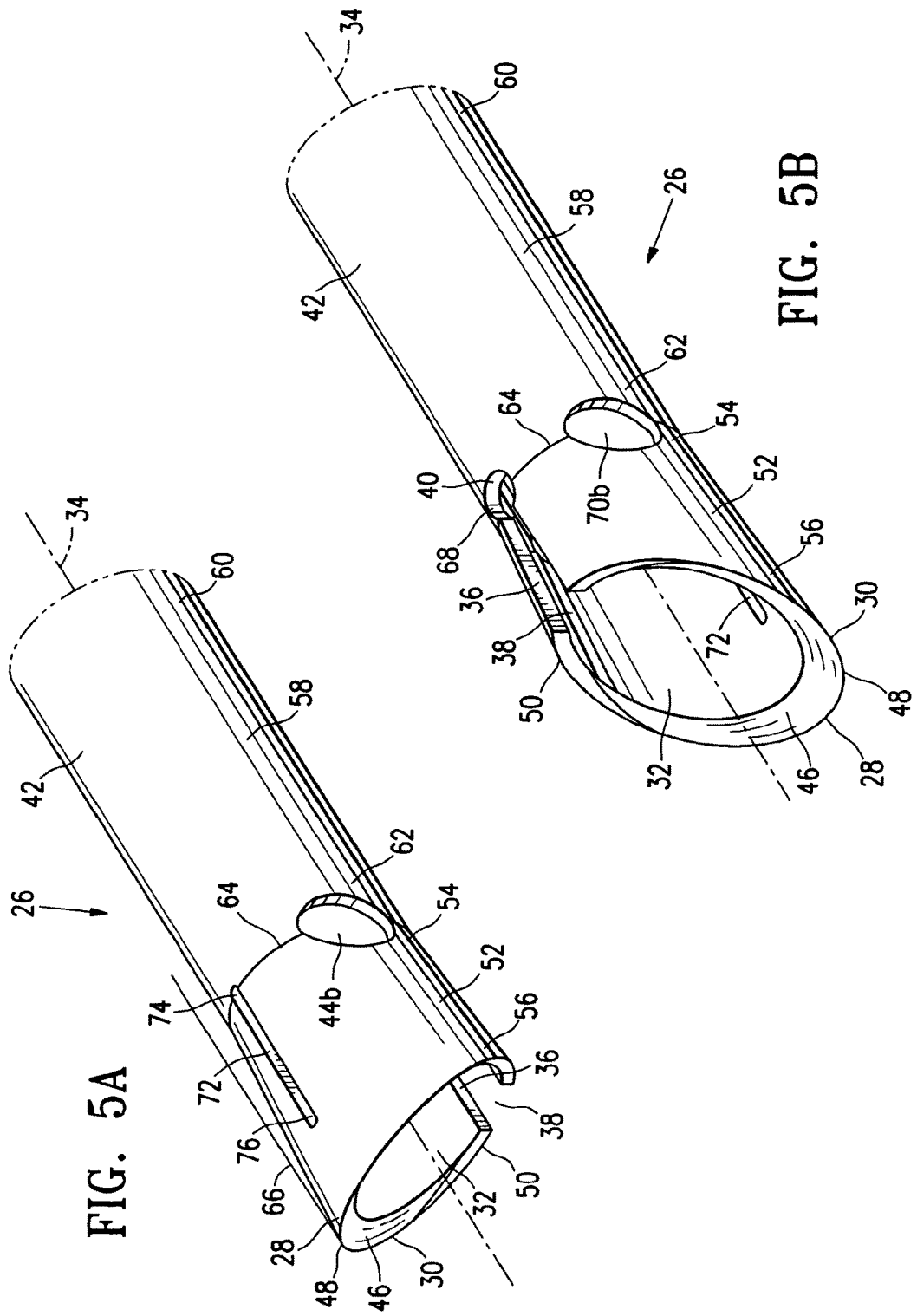

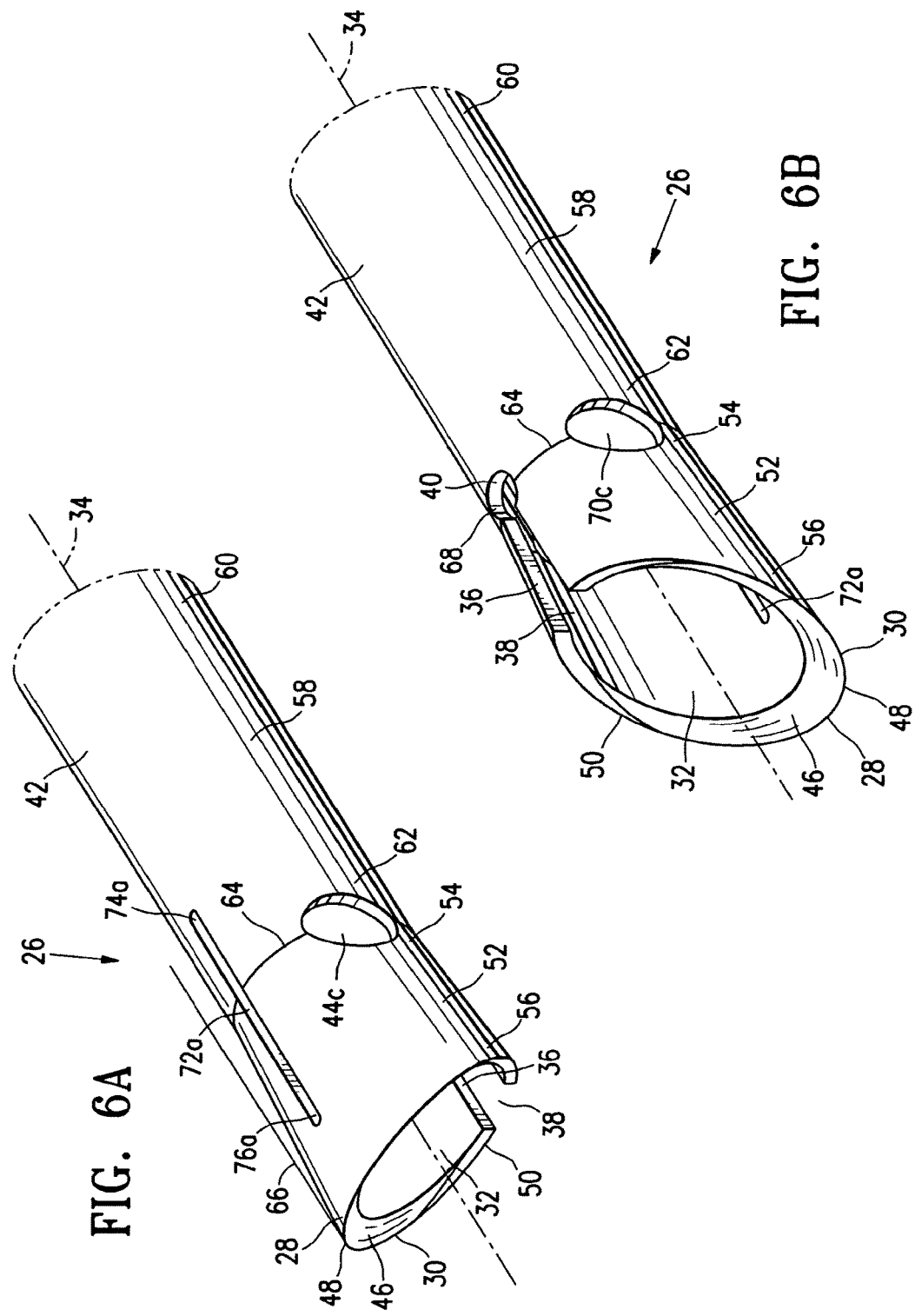

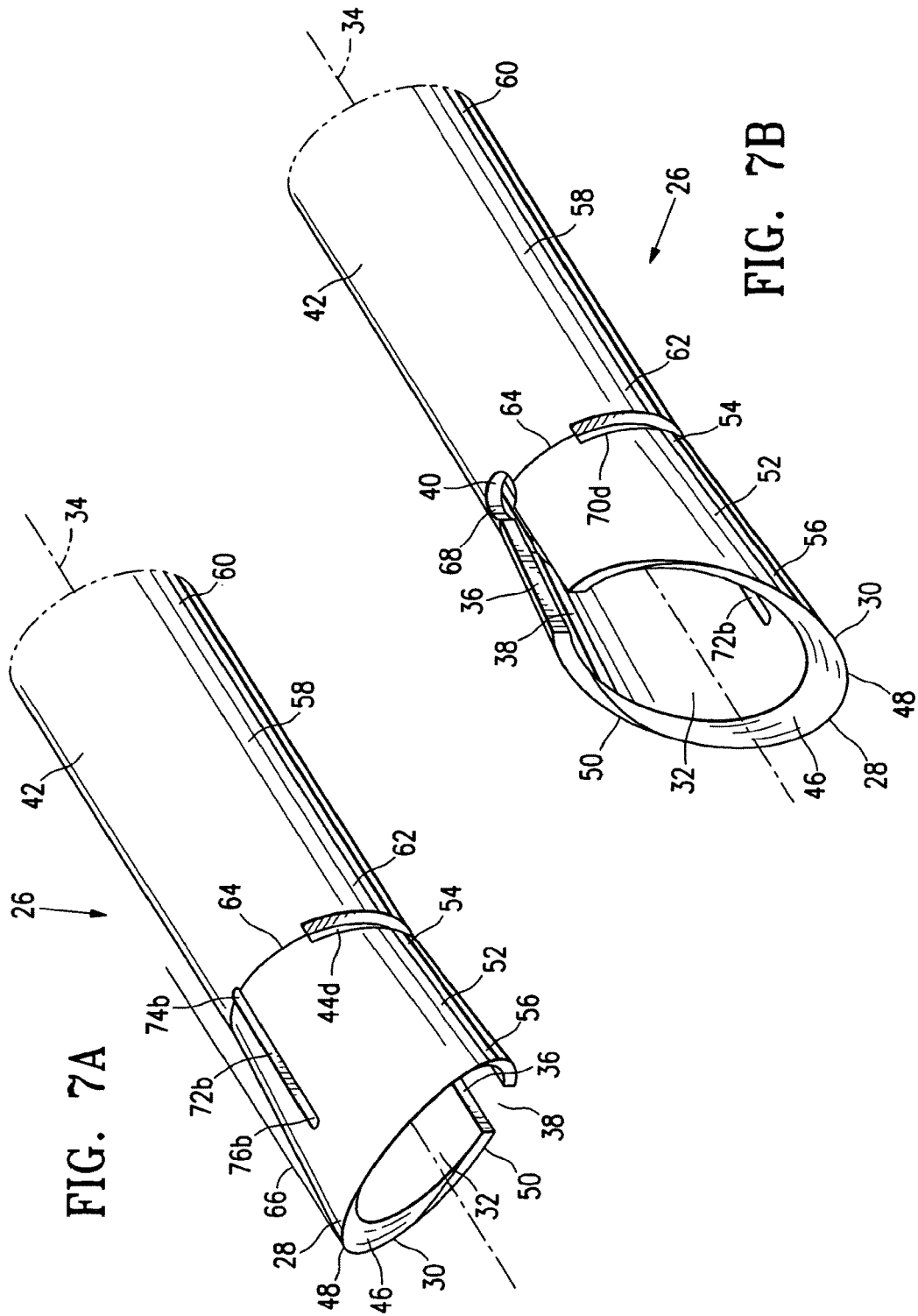

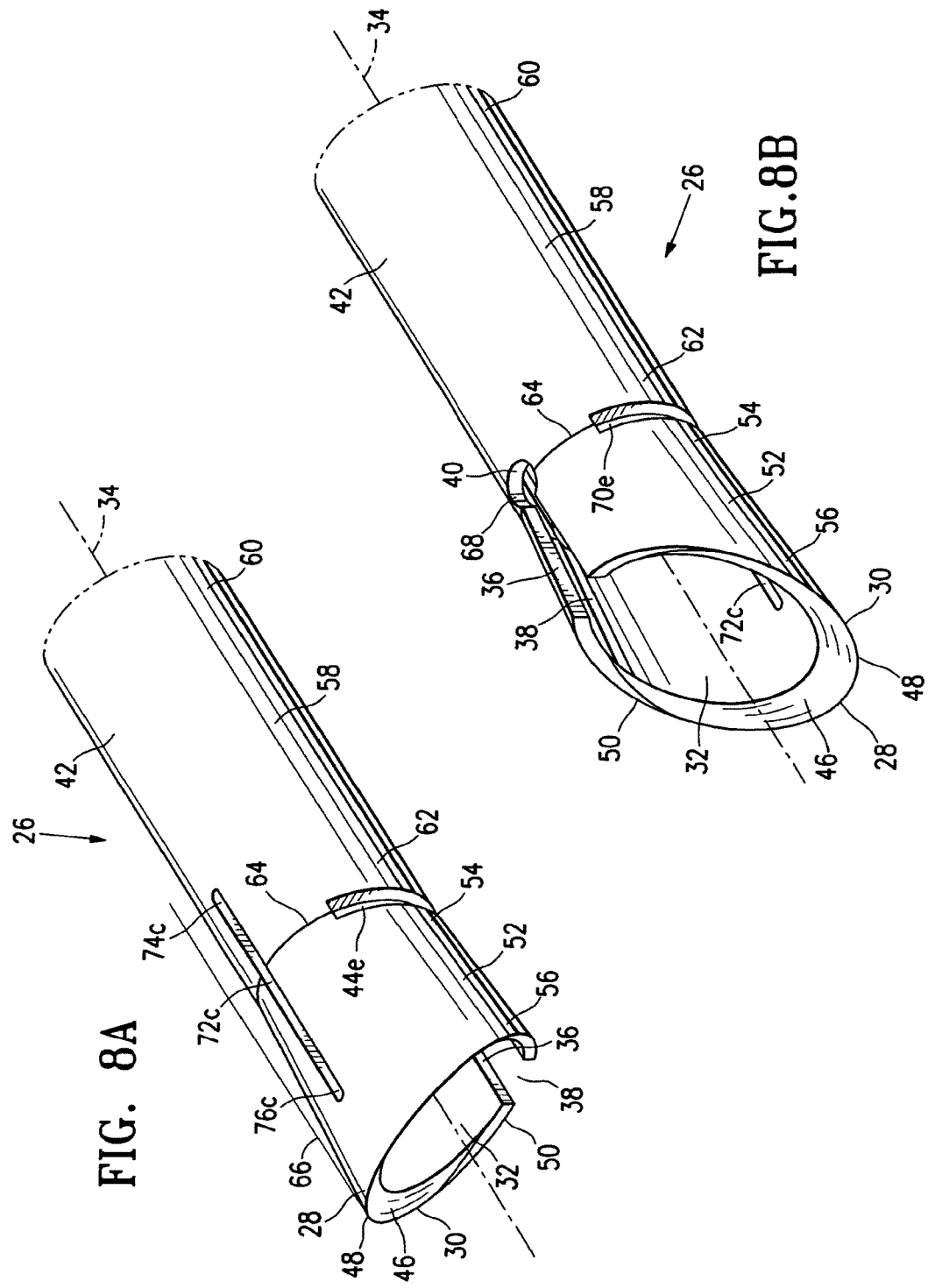

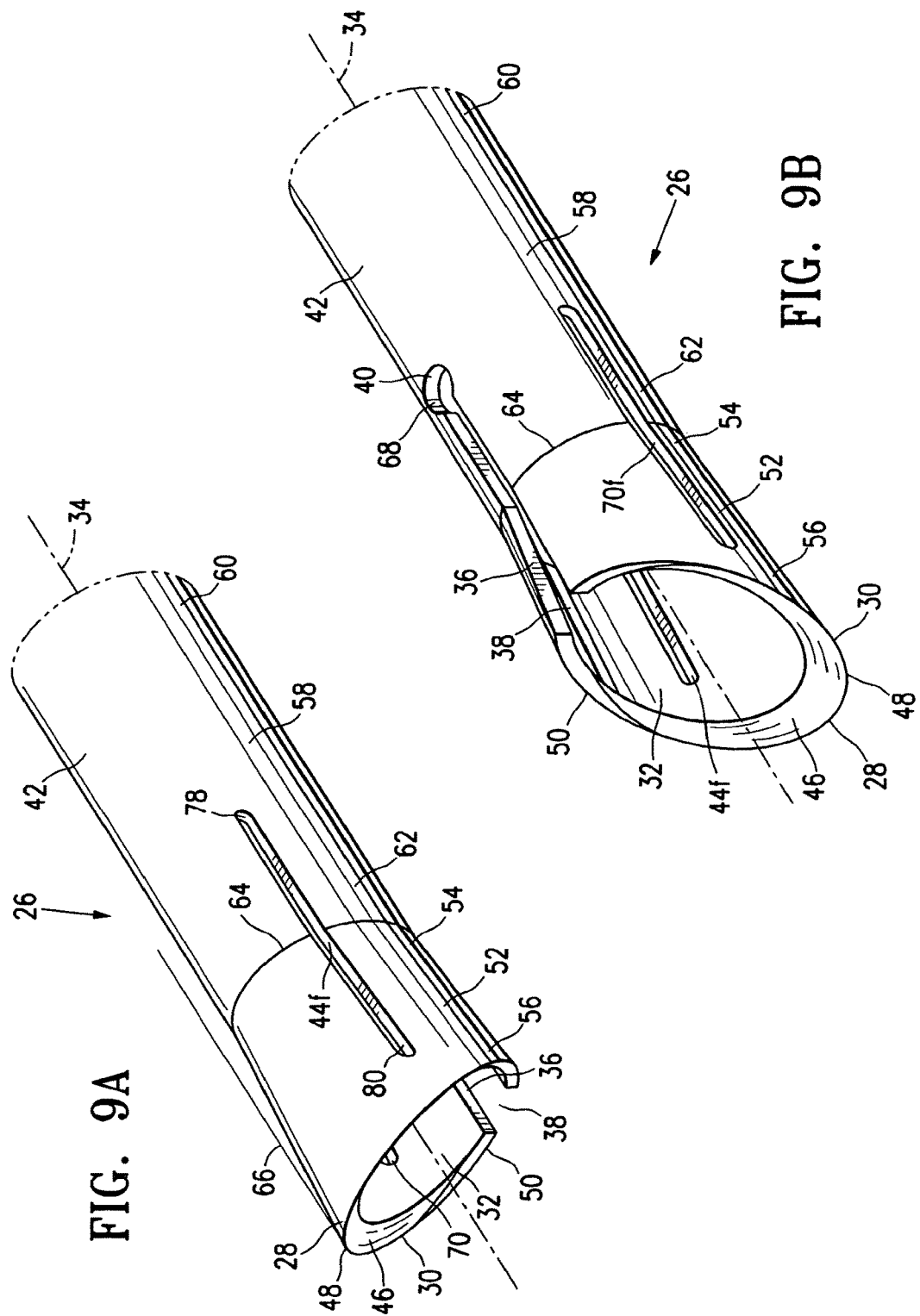

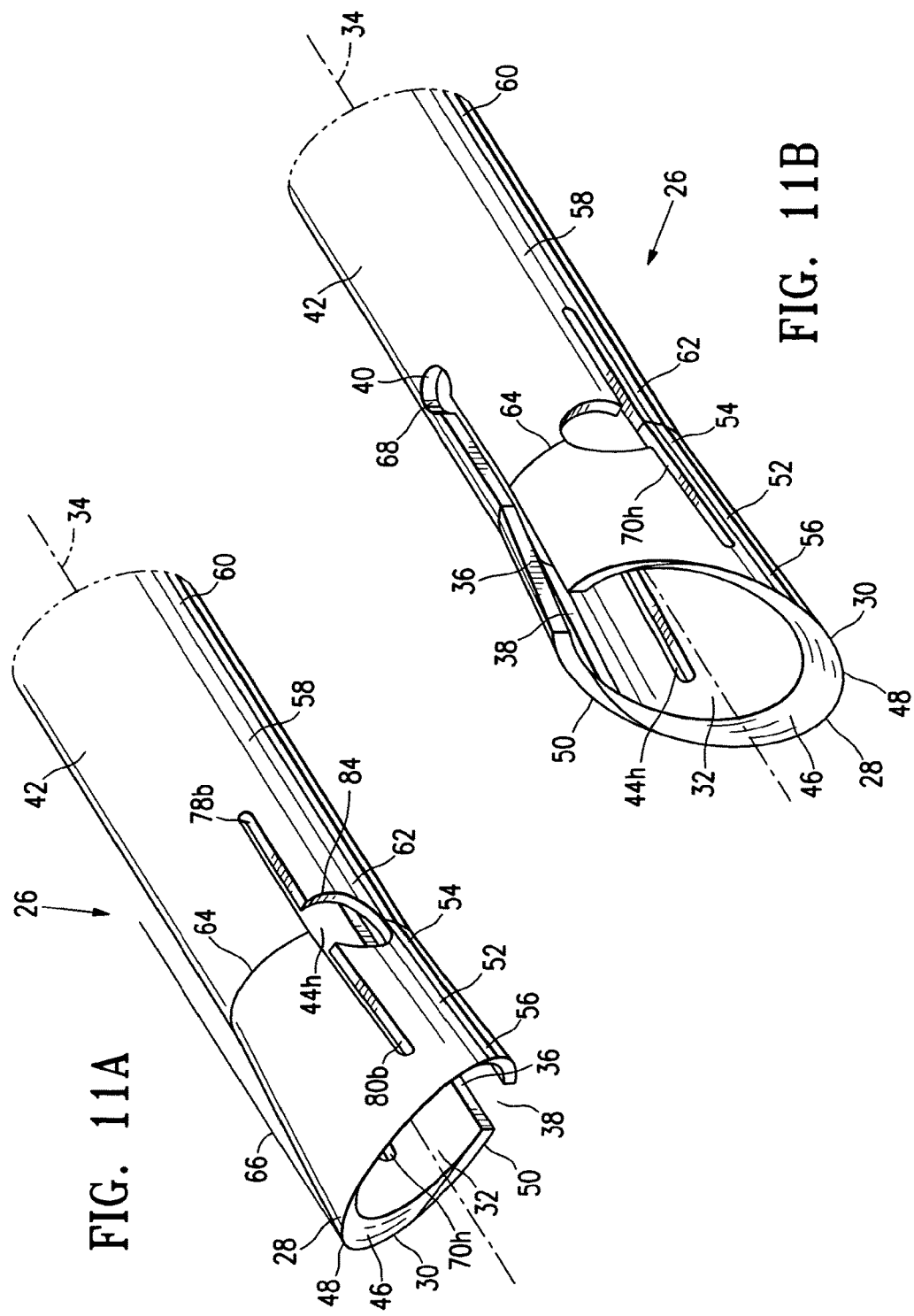

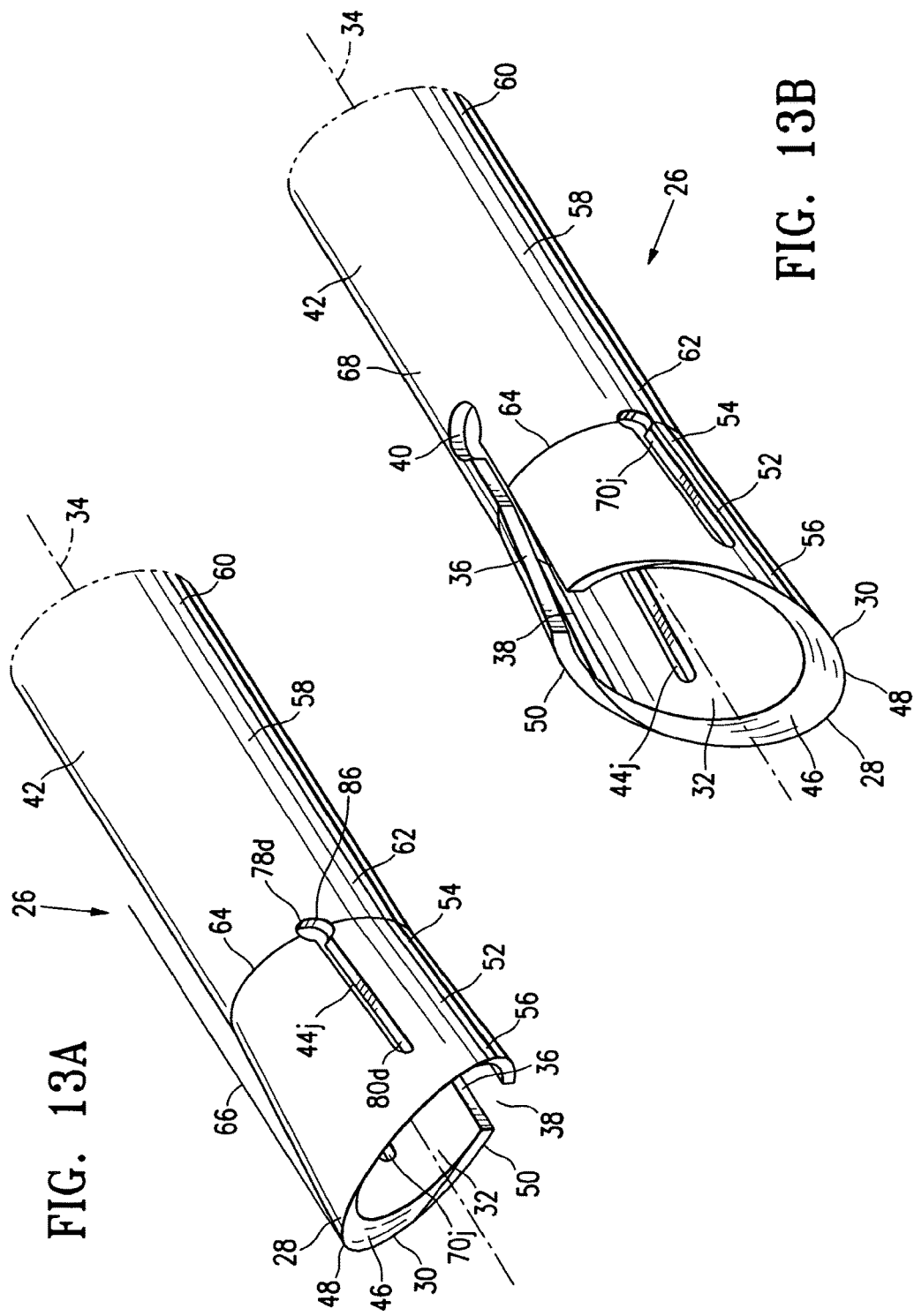

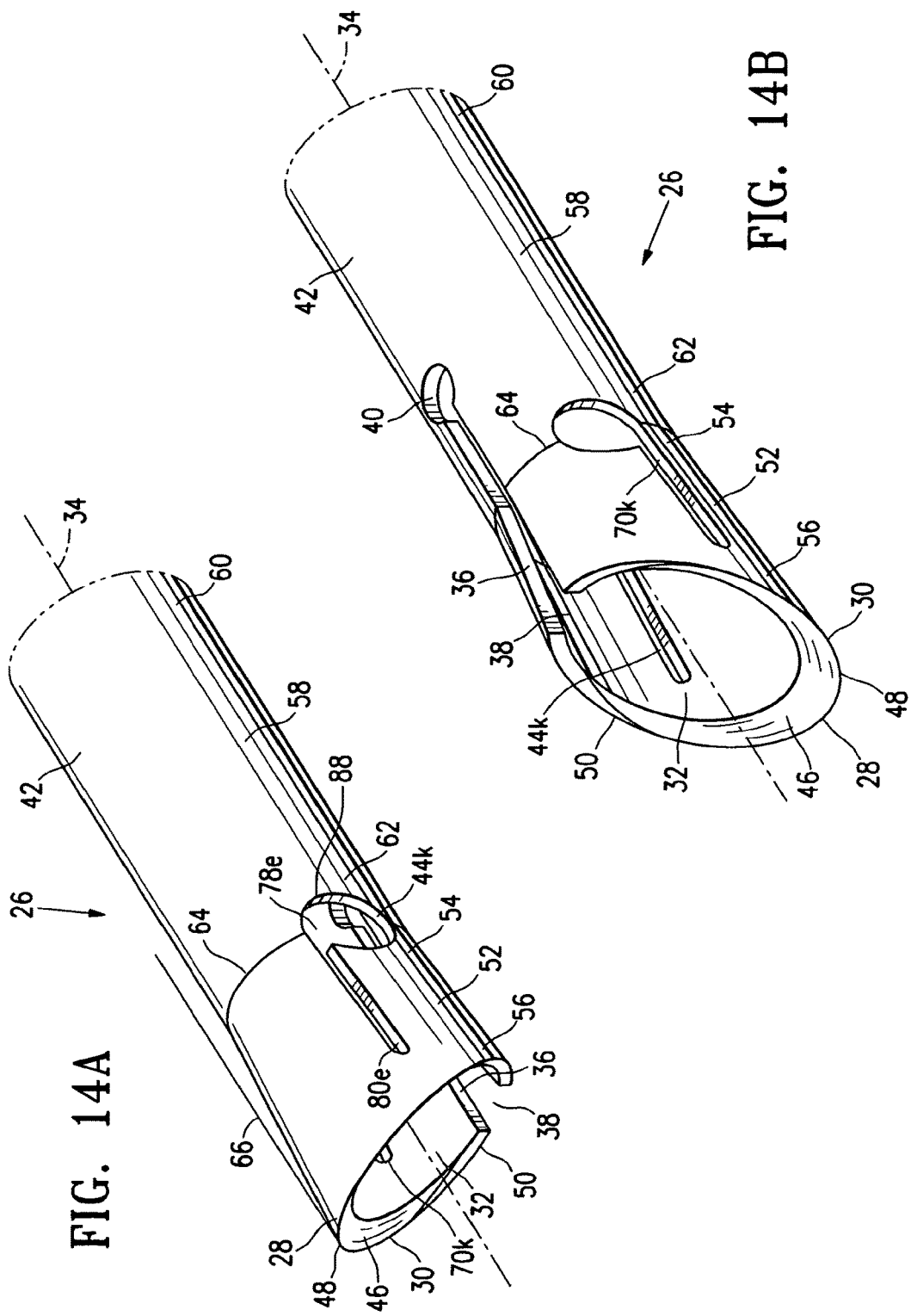

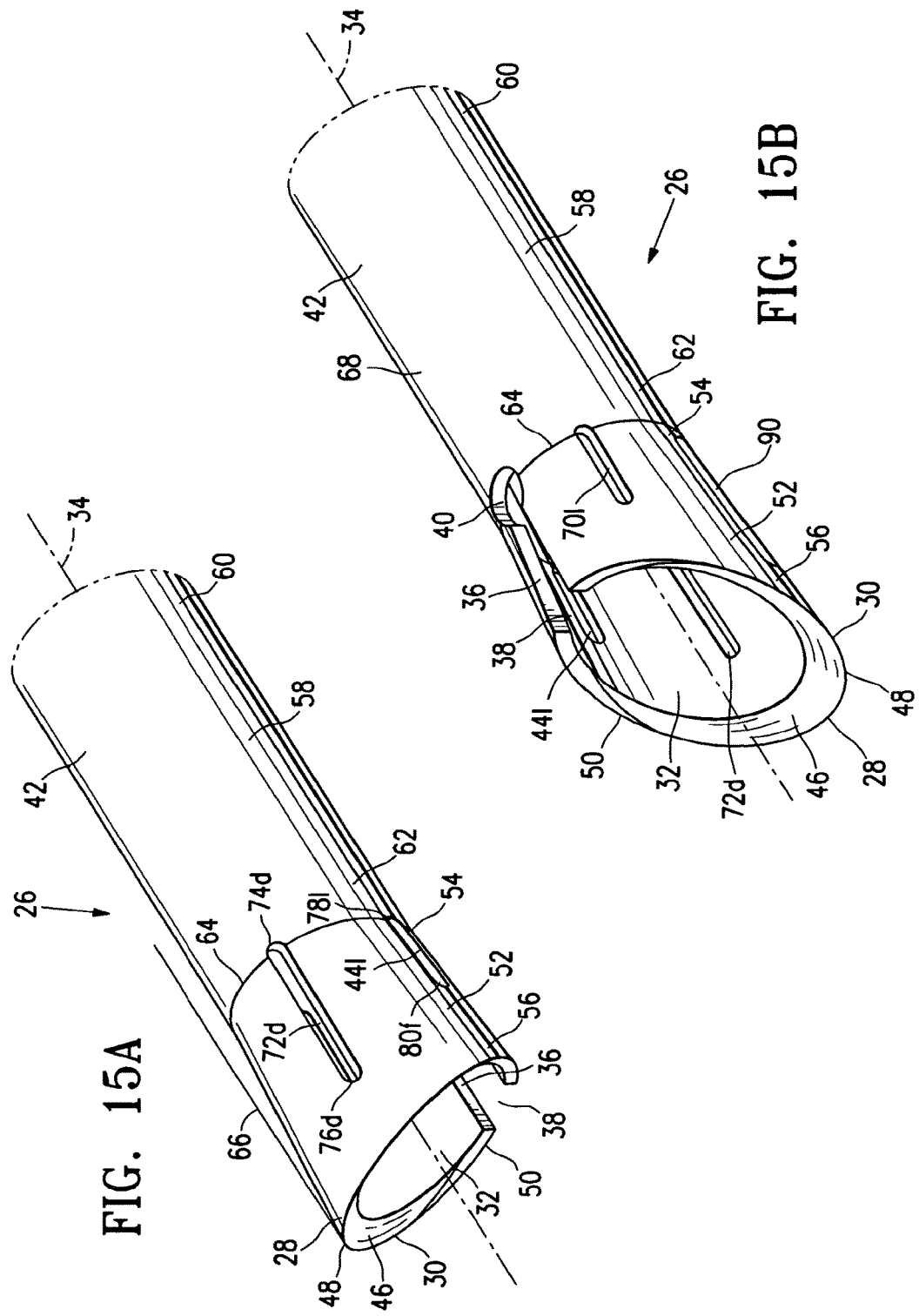

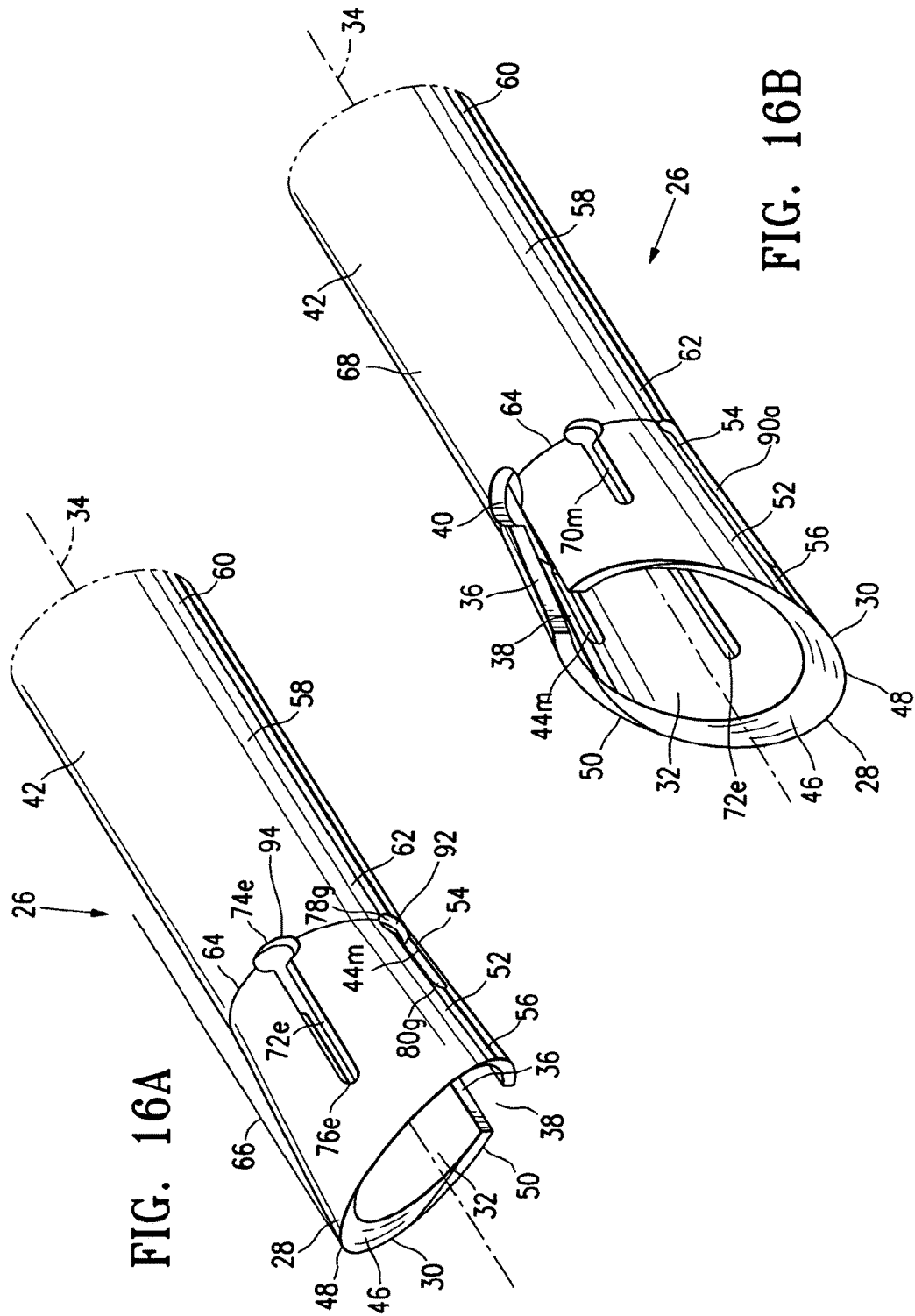

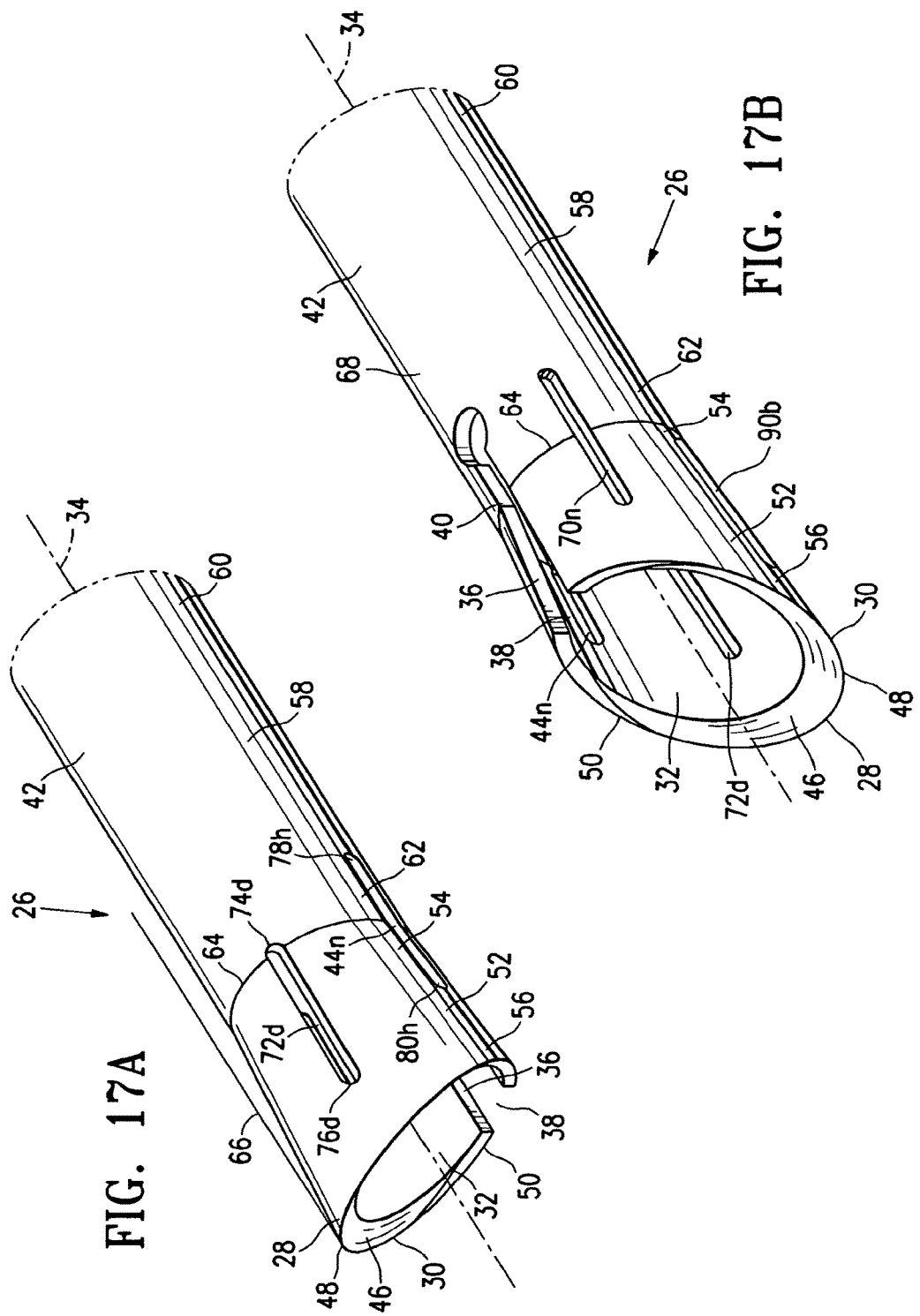

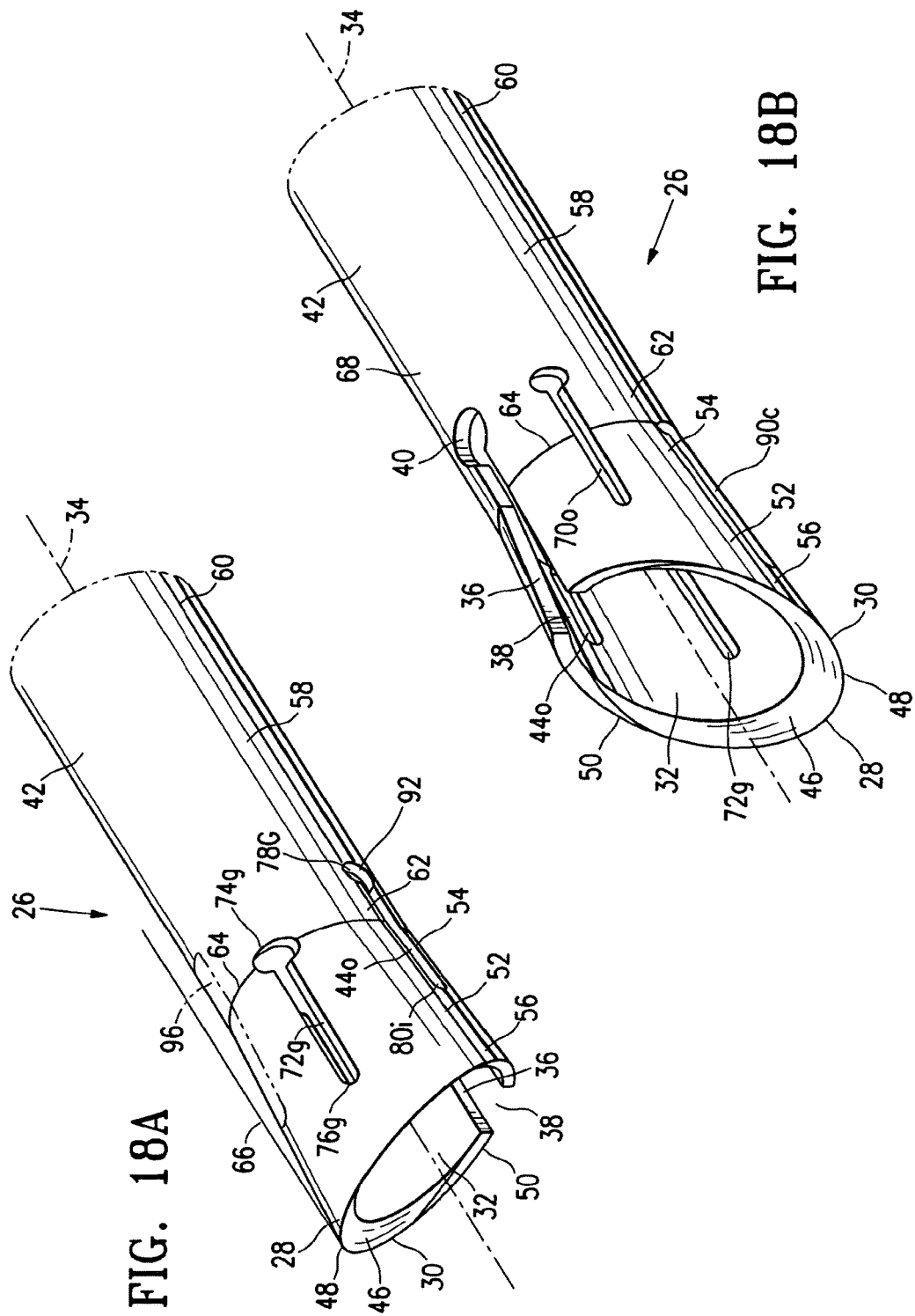

TISSUE CUTTING MEMBER FOR A BIOPSY DEVICE

RELATED APPLICATIONS

This application is a division of U.S. patent application Ser. No. 14/755,244, filed Jun. 30, 2015, which is a continuation of U.S. patent application Ser. No. 11/438,955, entitled "Tissue Cutting Member For A Biopsy Device", filed May 22, 2006, now U.S. Pat. No. 9,095,325, which claims the benefit of U.S. Provisional Application Ser. No. 60/683,584, filed on May 23, 2005, and claims priority therefrom, each of which is incorporated by reference herein in its entirety.

FIELD OF THE INVENTION

The present invention relates generally to tissue cutting members for tissue removing devices such as biopsy devices and the like.

BACKGROUND OF THE INVENTION

In diagnosing and treating certain medical conditions, such as potentially cancerous tumors, it is usually desirable to perform a biopsy, in which a specimen of the suspicious tissue is removed for pathological examination and analysis. In many instances, the suspicious tissue is located in a subcutaneous site, such as inside a human breast. To minimize surgical intrusion into the patient's body, it is desirable to be able to insert a small instrument into the patient's body to access the targeted site and to separate the biopsy specimen therefrom.

Tissue cutting members currently used with biopsy devices have a variety of problems. Often tissue becomes trapped between the cutting member and the shaft within which the cutting member is disposed. Also many cutting members currently available in the art are not suitable for effectively separating tough or hard tissue from the target site in a patient's body.

There is need in the art for cutting members with improved efficiency for separating tissue specimens from a target location in a patient's body.

SUMMARY OF THE INVENTION

This invention is directed to tissue cutting members for devices for separating tissue from a target site within a patient's body. More particularly, the invention is directed to tissue cutting members and biopsy devices using such tissue cutting members for the separation of a tissue specimen from supporting tissue at the targeted site within a patient. A suitable biopsy device having a cannula which may be utilized with a tissue cutting member having features of the invention is described in co-pending application Ser. No. 11/014,413, filed on Dec. 16, 2004.

A tissue cutting member embodying features of the invention includes a distal tubular portion having a distal tip with an outer tissue cutting edge, an inner tissue receiving aperture, and a longitudinal axis. Preferably the distal tip of the distal tubular portion has a beveled front face with a leading edge and a trailing edge.

The tubular distal tubular portion has a longitudinally oriented opening in a wall of the distal tubular portion with an open distal end which opens to the inner tissue receiving aperture, and a closed proximal end. The distal tubular portion of the tissue cutting member has at least a second opening in a wall of the tubular portion and preferably a plurality of openings circumferentially spaced from the open ended slot about the longitudinal axis and preferably the centers of these openings are circumferentially located at about 90°, 135°, or 180° from a midpoint of the longitudinally oriented opening. The one or more circumferentially spaced openings may be one of a variety of shapes, for example, a rectangular shape, a circular shape, or an elongated shape such as an oval or elongated slot. One or more of the openings in the distal tubular portion may be of one shape and one or more of the other openings may be of another shape. The openings allow for the vacuum to be maintained within the biopsy device when the cutting member is cutting and provide stress relief, facilitating radial expansion and/or contraction.

The distal tubular portion preferably has a flared distal section with a proximal end and a distal end, and a cylindrically shaped proximal section with a proximal end and a distal end. The open distal end of the longitudinally oriented opening facilitates the flaring of the flared distal section. The flared distal section ensures that the outer tissue cutting edge of the distal tubular portion engages an inner tissue cutting edge of a tissue receiving aperture in the cannula of the biopsy device to cleanly sever the tissue specimen from the supporting tissue and to provide a better tissue specimen for pathological examination.

These and other advantages of the invention will become more apparent from the following detailed description of the invention and the accompanying exemplary drawings.

BRIEF DESCRIPTION OF THE DRAWINGS

FIG. 3A is a perspective view of a distal tubular portion of a tissue cutting member embodying features of the invention including two openings with a rectangular shape.

FIG. 3B is a perspective view of the distal tubular portion shown in FIG. 3A that has been rotated 180° from the view of FIG. 3A.

FIG. 4A is a perspective view of a distal tubular portion of a tissue cutting member embodying features of the invention including two circular openings.

FIG. 4B is a perspective view of the distal tubular portion shown in FIG. 4A that has been rotated 180° from the view of FIG. 4A.

FIG. 5A is a perspective view of a distal tubular portion of a tissue cutting member embodying features of the invention including two circular openings and one opening which is an elongated longitudinally oriented slot.

FIG. 5B is a perspective view of the distal tubular portion shown in FIG. 5A that has been rotated 180° from the view of FIG. 5A.

FIG. 6A is a perspective view of a distal tubular portion of a tissue cutting member embodying features of the invention including two circular openings and one opening which is an elongated longitudinally oriented slot.

FIG. 6B is a perspective view of the distal tubular portion shown in FIG. 6A that has been rotated 180° from the view of FIG. 6A.

FIG. 7A is a perspective view of distal tubular portion of a tissue cutting member embodying features of the invention including two rectangular openings and one opening which is an elongated longitudinally oriented slot.

FIG. 7B is a perspective view of the distal tubular portion shown in FIG. 7A that has been rotated 180° from the view of FIG. 7A.

FIG. 8A is a perspective view of a distal tubular portion of a tissue cutting member embodying features of the invention including two rectangular openings and one opening which is an elongated longitudinally oriented slot.

FIG. 8B is a perspective view of the distal tubular portion shown in FIG. 8A that has been rotated 180° from the view of FIG. 8A.

FIG. 9A is a perspective view of a distal tubular portion of a tissue cutting member embodying features of the invention including two openings which are elongated longitudinally oriented slots.

FIG. 9B is a perspective view of the distal tubular portion shown in FIG. 9A that has been rotated. 180° from the view of FIG. 9A.

FIG. 11A is a perspective view of a distal tubular portion of a tissue cutting member embodying features of the invention including two openings which are elongated longitudinally oriented slots each having an enlarged circular shape between the proximal and distal ends thereof.

FIG. 11B is a perspective view of the distal tubular portion shown in FIG. 11A that has been rotated 180° from the view of FIG. 11A.

FIG. 13A is a perspective view of a distal tubular portion of a tissue cutting member embodying features of the invention including two openings which are elongated longitudinally oriented slots each having an enlarged circular shape at the proximal end thereof.

FIG. 13B is a perspective view of the distal tubular portion shown in FIG. 13A that has been rotated 180° from the view of FIG. 13A.

FIG. 14A is a perspective view of a distal tubular portion of a tissue cutting member embodying features of the invention including two openings which are elongated longitudinally oriented slots with an enlarged circular shape at the proximal end thereof.

FIG. 14B is a perspective view of the distal tubular portion shown in FIG. 14A that has been rotated 180° from the view of FIG. 14A.

FIG. 15A is a perspective view of a distal tubular portion of a tissue cutting member embodying features of the invention including four openings which are elongated longitudinally oriented slots.

FIG. 15B is a perspective view of the distal tubular portion shown in FIG. 15A that has been rotated 180° from the view of FIG. 15A.

FIG. 16A is a perspective view of a distal tubular portion of a tissue cutting member embodying features of the invention including four openings which are elongated longitudinally oriented slots each having an enlarged circular shape at the proximal end thereof.

FIG. 16B is a perspective view of the distal tubular portion shown in FIG. 16A that has been rotated 180° from the view of FIG. 16A.

FIG. 17A is a perspective view of a distal tubular portion of a tissue cutting member embodying features of the invention including four openings which are elongated longitudinally oriented slots.

FIG. 17B is a perspective view of the distal tubular portion shown in FIG. 17A that has been rotated 180° from the view of FIG. 17A.

FIG. 18A is a perspective view of a distal tubular portion of a tissue cutting member embodying features of the invention including four openings which are elongated longitudinally oriented slots each having an enlarged essentially circular shape at the proximal end thereof.

FIG. 186 is a perspective view of the distal tubular portion shown in FIG. 18A that has been rotated 180° from the view of FIG. 18A.

DETAILED DESCRIPTION OF THE INVENTION

Figure 1:
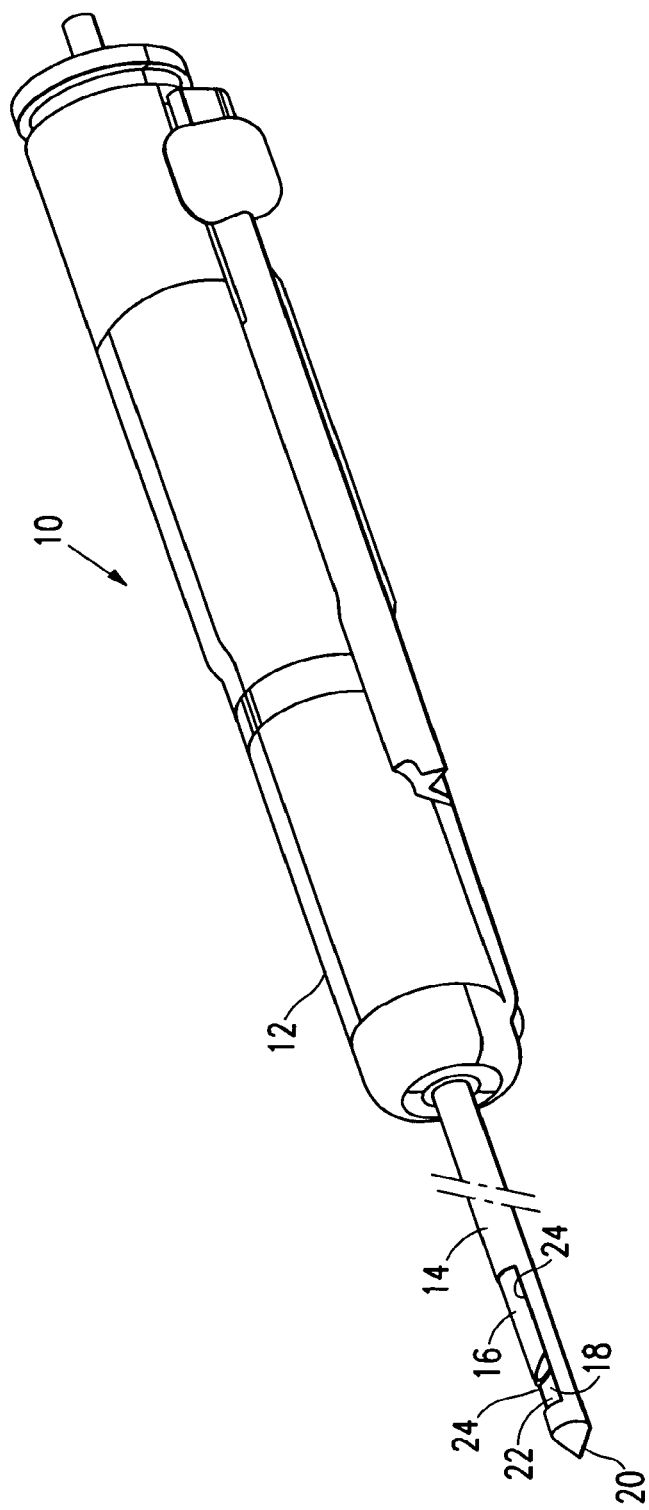
FIG. 1 is a perspective view of the proximal portion of an elongated probe member of a biopsy device that has features of the invention.

FIG. 1 shows an embodiment of a probe component 10 including a housing 12 and an outer tubular member or cannula 14. The tissue cutting member 16 embodying features of the invention is slidably disposed within an inner lumen 18 in the cannula 14. The probe component 10 may be part of a biopsy device such as that described in co-pending application Ser. No. 11/014,413 filed on Dec. 16, 2004. Details of the probe component 10 and other parts of the biopsy device may be found in the aforesaid application.

Figure 2:
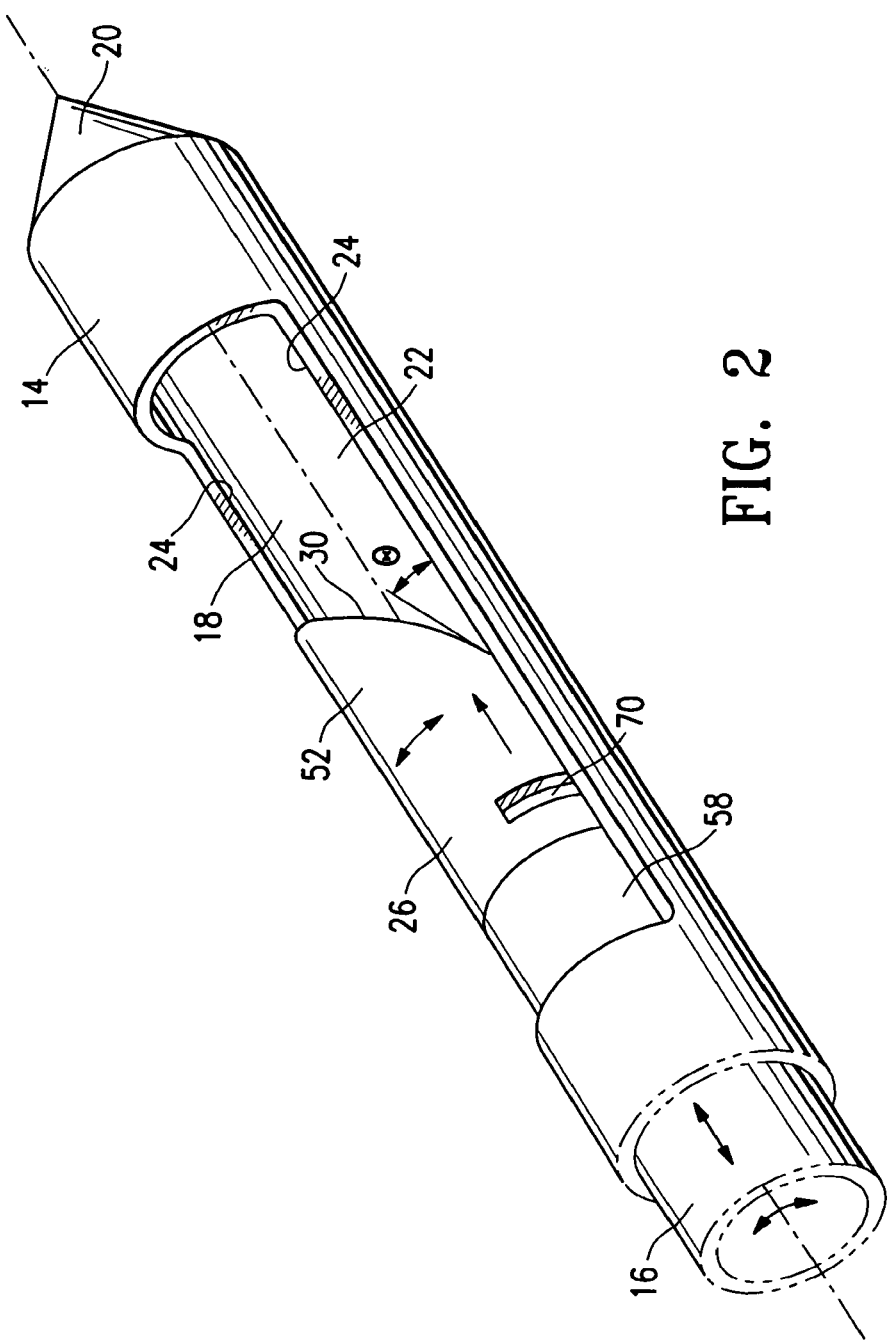
FIG. 2 is an enlarged perspective view of a distal portion of the elongated probe shown in FIG. 1 illustrating a tissue cutting member embodying features of the invention disposed within the probe.
Figure 3E:
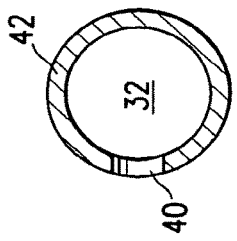
FIG. 3E is a transverse cross sectional view of the distal tubular portion taken along lines 3E-3E in FIG. 3C.
Figure 3F:
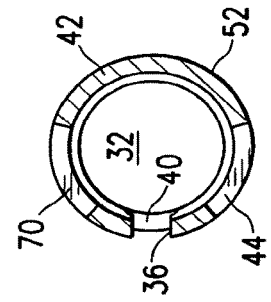
FIG. 3F is a transverse cross sectional view of the distal tubular portion taken along lines 3F-3F.
Figure 3C:
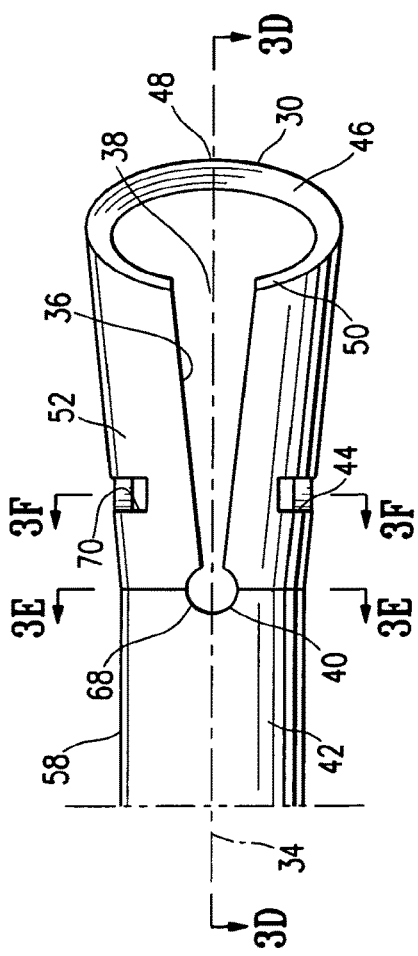
FIG. 3C is an elevational view of the embodiment of the device shown in FIG. 3A.
Figure 3D:
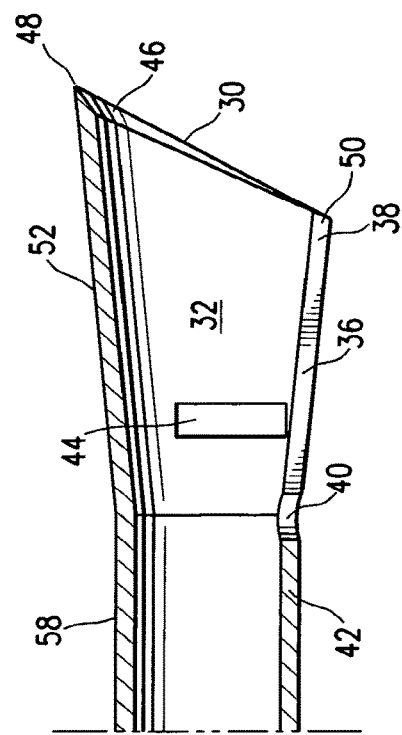
FIG. 3D is a longitudinal cross sectional view of the distal tubular portion taken along lines 3D-3D in FIG. 3C.

The cannula 14 of the probe component 10 has a distal tip 20 and an open tissue receiving aperture 22 spaced proximal to the distal tip 20. The tissue receiving aperture 22 has an inner tissue cutting edge 24. The tissue cutting member 16 is slidably disposed within the inner lumen 18 of the cannula 14 of the probe component, as shown in FIG. 2.

The distal tip 20 of the cannula 14 may have a variety of tip shapes. The shape of the tissue penetrating distal tip disclosed in the above referenced co-pending application Ser. No. 11/014,413 has been found to be suitable for penetrating tissue, particularly breast tissue. Alternatively, the distal tip 20 may have an arcuate RF electrode such as disclosed in U.S. Pat. Nos. 6,261,241 and 6,471,700, (all of which have been assigned to the present assignee) that facilitate advancement of the probe through tissue.

FIGS. 3A-18B show tissue cutting member 16 having features of the invention including a distal tubular portion 26. Preferably the tubular distal portion has a diameter of between about 0.1 inches and 0.2 inches. The distal tubular portion 26 has a distal tip 28 with an outer tissue cutting edge 30 and an inner tissue receiving aperture 32 and a longitudinal axis 34. The distal tubular portion 26 also includes a longitudinally oriented opening 36 that has an open distal end 38 which opens to the inner tissue receiving aperture 32 and which has a closed proximal end 40. Preferably the longitudinally oriented opening 36 has a length of about 0.1 inches to about 0.3 inches. Additionally, a wall 42 of the tubular distal portion 26 has at least a second opening 44 (shown having a rectangular shape in FIGS. 3A-3F) which is circumferentially spaced from the longitudinally oriented opening 36 about the longitudinal axis 34.

Preferably the distal tip 28 of the distal tubular portion 26 has a beveled front face 46 with a leading edge 48 and a trailing edge 50. The longitudinally oriented opening 36 in distal tubular portion 26 opens to the trailing edge 50 of the beveled front face 46.

The distal tubular portion 26 preferably includes a flared distal section 52 which has a proximal end 54 and a distal end 56 and a cylindrically shaped proximal section 58 which has a proximal end 60 and a distal end 62. The distal tubular portion 26 may have a junction 64 where the proximal end 54 of the flared distal section 52 meets the distal end 62 of the cylindrically shaped proximal section 58. Preferably the flared distal section flares outward about 1° to 3° degrees from the cylindrically shaped proximal section. The open distal end 38 of the longitudinally oriented opening 36 facilitates the flaring of the flared distal section 52 as shown by line 66. The flared distal section 52 ensures that the outer tissue cutting edge 30 of the distal tubular portion 26 engages the inner tissue cutting edge 24 of the tissue receiving aperture 22, as shown in FIG. 2, to provide scissor-like cutting motion for separating a tissue specimen from supporting tissue at the target biopsy site.

The longitudinally oriented opening 36 preferably has an enlarged essentially circular shape 68 at the closed proximal end 40 of the longitudinally oriented opening 36. The closed proximal end 40 of the longitudinally oriented opening 36 can be located entirely within the flared distal section 52 (not shown), entirely within in the cylindrically shaped proximal section 58 as shown in FIGS. 9A-14B and 17A-18B, or at least Partially in the distal end 62 of the cylindrically shaped proximal section 58 as shown in FIGS. 3A-8B and 15A-16B.

The second opening 44 (shown with a rectangular shape in FIGS. 3A-3F) in the wall 42 of the tubular distal portion 26 allows for a vacuum to be maintained within the probe component 10. Preferably the distal tubular portion 26 has a plurality of openings. The openings of the distal tubular portion are circumferentially disposed at an angle about the longitudinal axis 34 and the centers of these openings are preferably circumferentially located at about 90°, 135°, or 180° from a midpoint of the longitudinally oriented opening 36. Preferably a third opening 70 (shown with a rectangular shape in FIGS. 3A-3F) is provided in the wall 42 of the distal tubular portion 26 circumferentially spaced from the longitudinally oriented opening 36 and essentially opposite of the second opening 44. The second opening 44 may have a variety of shapes for example, a rectangular shape, a circular shape, or an elongated shape such as an oval or elongated slot. Preferably when the second opening 44 is an elongated slot, the opening has a length of between about 0.1 inches and 0.4 inches. The second opening 44 and the third opening 70 preferably have the same shape, however, one or more of the openings may be of one shape and one or more of the other openings may be of another shape.

In one embodiment of the device having features of the invention, shown in FIGS. 3A-3E, the second and third openings 44 and 70 of the distal tubular portion 26 are circumferential rectangular openings. In this embodiment the longitudinal midlines of the second opening 44 and the third opening 70 lie in a plane perpendicular to the longitudinal axis 34 and are located in the flared distal section 52 of the distal tubular portion 26. The closed proximal end 40 of the longitudinally oriented opening 36 is at the proximal end 54 of the flared distal section 52.

FIGS. 4A and 4B show a cutting member 16 which embodies features of the invention wherein the second opening 44a and third opening 70a of the distal tubular portion 26 are circular openings and are located in the flared distal section 52. The closed proximal end 40 of the longitudinally oriented opening 36 is located at least partially in the distal end 62 of the cylindrically shaped proximal section 58.

FIGS. 5A and 5B show a distal tubular portion 26 of the tissue cutting member 16 wherein the second opening 44b and third opening 70b are circular openings located at least partially in the distal end 62 of the cylindrically shaped proximal portion 58. The closed proximal end 40 of the longitudinally oriented opening 36 is located at the proximal end 54 of the flared distal section 52.

The distal tubular portion 26 in FIGS. 5A and 5B also includes a fourth opening 72 which is an elongated longitudinally oriented slot with a closed proximal end 74 and a closed distal end 76. The fourth opening 72 is opposite to the longitudinally oriented opening 36. The closed proximal end 74 of the opening 72 is located at the proximal end 54 of the flared distal section 52. The closed distal end 76 of the fourth opening 72 is located in the flared distal section 52.

FIGS. 6A and 6B show a tissue cutting member 10 wherein the distal tubular portion 26 has a second opening 44c and a third opening 70c which are located at least partially in the distal end 62 of the cylindrically shaped section 58. FIGS. 6A and 6B also include a fourth opening 72a which is an elongated longitudinally oriented slot with a closed proximal end 74a and a closed distal end 76a. The closed proximal end 74a of the fourth opening 72a is in the cylindrically shaped proximal section 58 and the closed distal end 76a of the fourth opening 72a is in the flared distal section 52.

In the embodiment of the device having features of the invention shown in FIGS. 7A and 7B, the second opening 44d and the third opening 70d of the distal tubular portion 26 have a rectangular shape and are oriented perpendicular to the longitudinal axis 34. The closed proximal end 40 of the longitudinally oriented opening 36 and the second 44d and third 70d openings are located at least partially in the distal end 62 of the cylindrically shaped proximal section 58.

FIGS. 7A and 7B also include fourth opening 72b which is an elongated longitudinally oriented slot with a closed proximal end 74b and a closed distal end 76b. The closed proximal end 74b of the fourth opening 72b is located at the proximal end 54 of the flared distal section 52. The closed distal end 76b of the fourth opening 72b is located in the flared distal section 52.

FIGS. 8A and 8B show a distal tubular portion 26 of the tissue cutting member 16 which has a second opening 44e and a third opening 70e which have a rectangular shape and are oriented perpendicular to the longitudinal axis 34. The second 44e and third 70e openings are located at least partially in the distal end 62 of the cylindrically shaped proximal section 58. FIGS. 8A and 8B also include a fourth opening 72c which is an elongated longitudinally oriented slot with a closed proximal end 74c and a closed distal end 76c. The closed proximal end 74c of the fourth opening 72c is located in the cylindrically shaped proximal section 58 and the closed distal end 76c of the fourth opening 72c is located in the flared distal section 52. In this embodiment the closed proximal end 40 of the longitudinally oriented opening 36 is located at least partially in the distal end 62 of the cylindrically shaped proximal section 58.

In the embodiment of the device having features of the invention shown in FIGS. 9A and 9B, the second opening 44f of the tubular distal portion 26 is an elongated longitudinally oriented slot with a closed proximal end 78 and a closed distal end 80. The closed proximal end 78 is located in the cylindrically shaped proximal section 58. The closed distal end 80 of the second opening 44f is located in the flared distal section 52. The third opening 70f is has the same shape as the second opening 44f and the same orientation with respect to the flared distal section 52 and the cylindrically shaped proximal section 58. In this embodiment the closed proximal end 40 of the longitudinally oriented opening 36 is located in the cylindrically shaped proximal section 58.

Figures 10A, 10B:
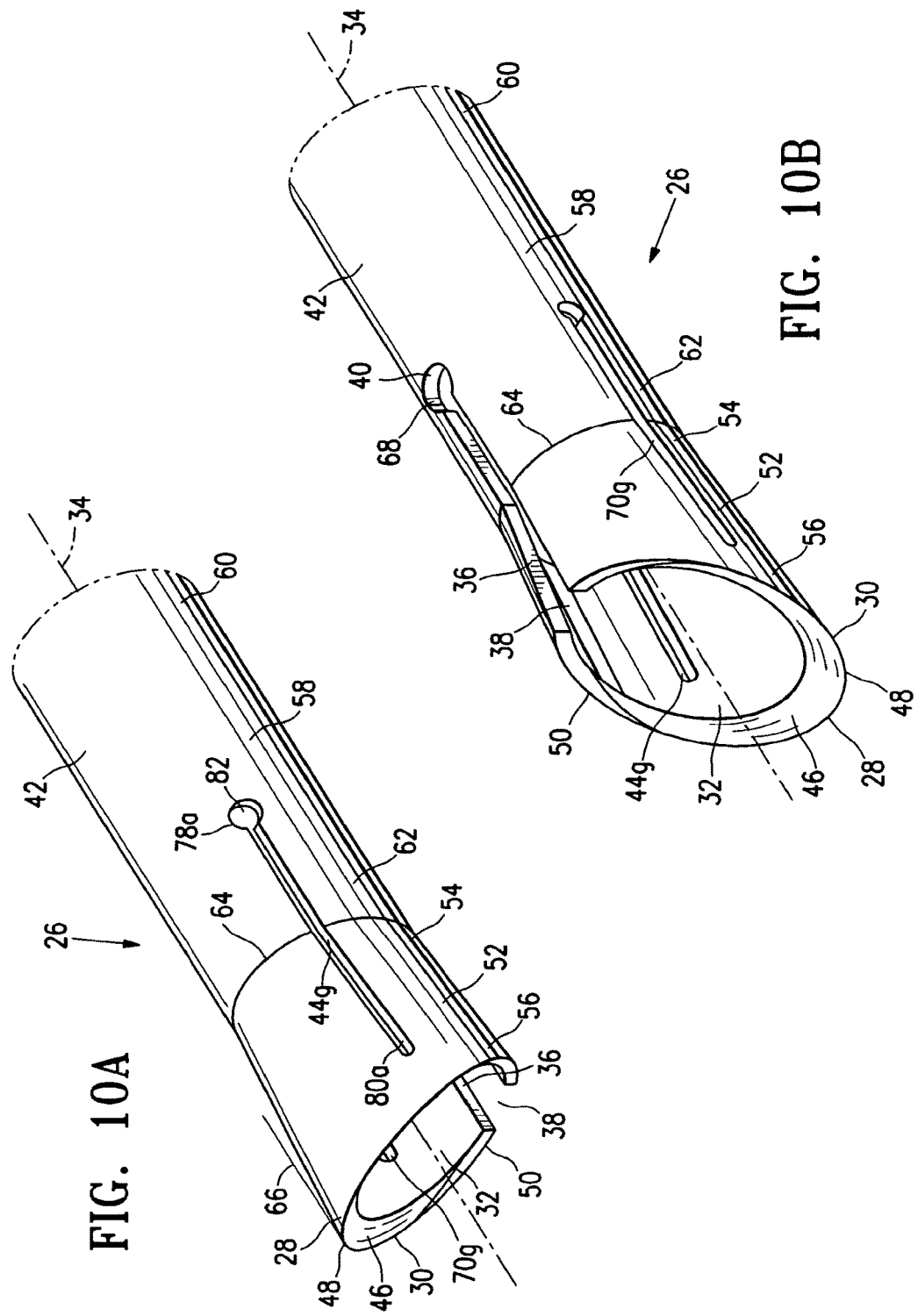
FIG. 10A is a perspective view of a distal tubular portion of a tissue cutting member embodying features of the invention including two openings Which are elongated longitudinally oriented slots with an enlarged circular shape at the proximal end thereof.
FIG. 10B is a perspective view of the distal tubular portion shown in FIG. 10A that has been rotated 180° from the view of FIG. 10A.

FIGS. 10A and 10B show a distal tubular portion 26 of the tissue cutting member wherein the closed proximal end 40 of the longitudinally oriented opening 36 is in the cylindrically shaped proximal section 54 of the distal tubular portion 26. The distal tubular portion 26 has a second opening 44g which is an elongated longitudinally oriented slot with a closed distal end 80a and a closed proximal end 78a and an enlarged essentially circular shape 82 at the proximal end 78a thereof. The closed proximal end 78a of the second 44g opening is located in the cylindrically shaped proximal section 58 and the closed distal end 80a of second opening is located in the flared distal section 52. The third opening 70g of the distal tubular portion 26 has the same shape as the second opening 44g and has the same orientation.

FIGS. 11A and 11B show a distal tubular portion 26 of the tissue cutting member 16 wherein the distal tubular portion 26 has a second opening 44h which is an elongated longitudinally oriented slot with a closed proximal end 78b and a closed distal end 80b. The second opening also had an enlarged essentially circular shape 84 located between the proximal 78b and distal 80b ends. The closed proximal end 78b of the elongated shape is in the cylindrically shaped proximal section 58 and the closed distal end 80b of the elongated shape is in the distal flared section 52. The enlarged essentially circular shape 84 of the second opening 44h is at least partially in the distal end 62 of the cylindrically shaped proximal section 58. The third opening 70h is the same shape as the second opening 44h and has the same orientation as the second opening 44h. In this embodiment the closed proximal end 40 of the longitudinally oriented opening 36 is in the cylindrically shaped proximal section 58 of the distal tubular portion 26.

Figures 12A, 12B:
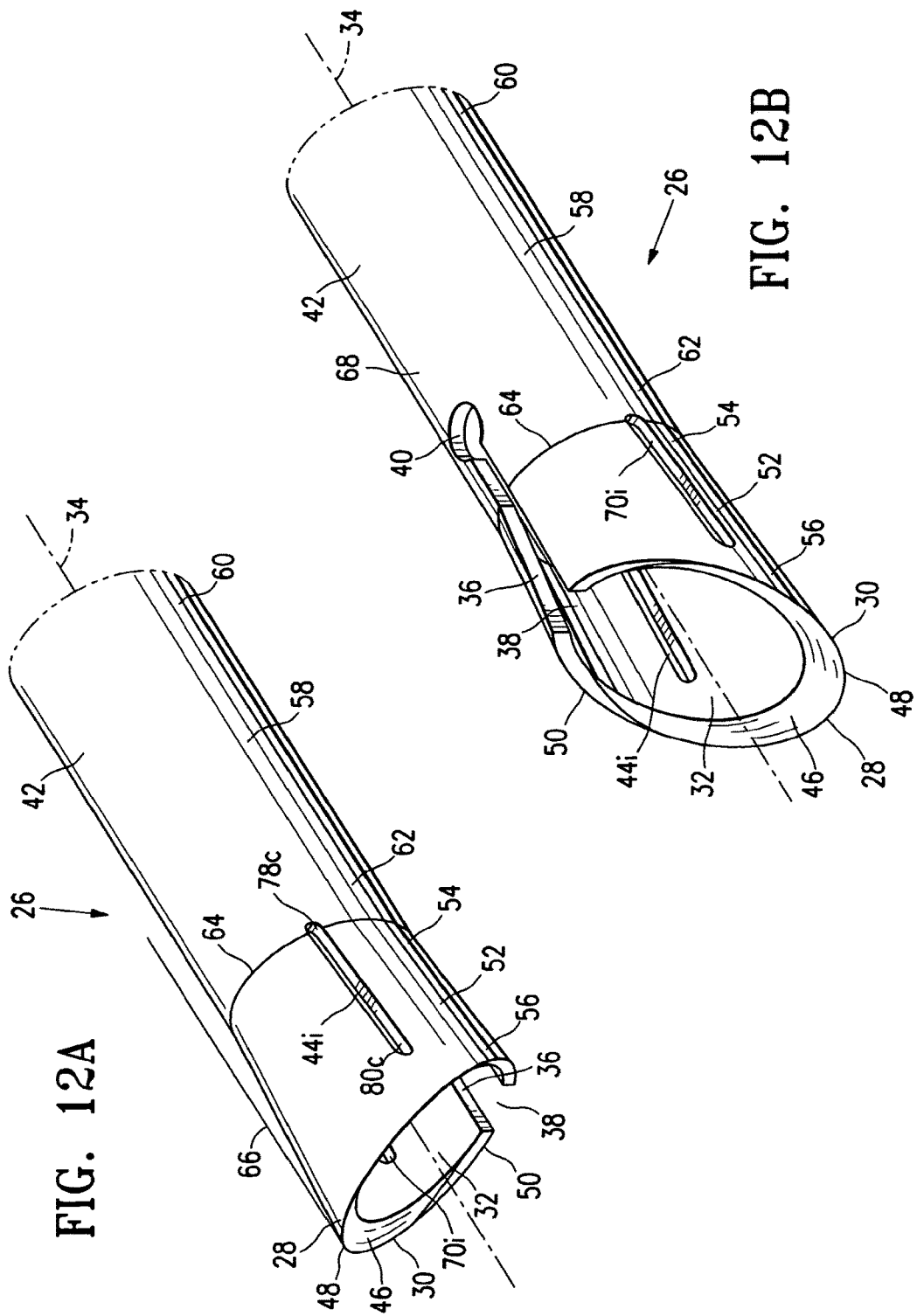
FIG. 12A is a perspective view of a distal tubular portion of a tissue cutting member embodying features of the invention including two openings which are elongated longitudinally oriented slots.
FIG. 12B is a perspective view of the distal tubular portion shown in FIG. 12A that has been rotated 180° from the view of FIG. 12A.

FIGS. 12A and 12B show a distal tubular portion of the tissue cutting member 26 wherein the closed proximal end 40 of the longitudinally oriented opening 36 is in the cylindrically shaped proximal section 58 of the distal tubular portion 26. The second opening 44i is an elongated longitudinally oriented slot with a closed proximal end 78c and a closed distal end 80c. The closed proximal end 78c of the first opening 44i is located at the proximal end 54 of the flared distal section 52. The closed distal end 80c of the second opening 44i is located in the flared distal section 52. The third opening 70i has the same shape and orientation as the second opening 44i.

FIGS. 13A and 13B show a distal tubular portion 26 of the tissue cutting member 16, which has a second opening 44j which is an elongated longitudinally oriented slot with a closed distal 80d end and closed proximal end 78d. The closed proximal end 78d has an enlarged essentially circular shape 86. The closed distal end 80d of the second opening 44j is located in the flared distal section 52 and the closed proximal end 78d is located at least partially in the distal end 62 of the cylindrically shaped proximal section 58. The third opening 70j has the same shape and orientation as the second opening 44j. In this embodiment the closed proximal end 40 of the longitudinally oriented opening 36 is in the cylindrically shaped proximal section 58 of the distal tubular portion 26.

FIGS. 14A and 14B show a distal tubular portion 26 of the tissue cutting member 16 which has a second opening 44k which is an elongated longitudinally oriented slot with a closed proximal end 78e and a closed distal end 80e. The closed proximal end 78e of the elongated slot has an enlarged essentially circular shape 88 which extends toward the longitudinally oriented opening 36. In this embodiment the closed proximal end 40 of the longitudinally oriented opening 36 is in the cylindrically shaped proximal section 58 of the distal tubular portion 26.

FIGS. 15A and 15B show a distal tubular portion 26 of the tissue cutting member 16 wherein closed proximal end 40 of the longitudinally oriented opening 36 is located at least partially in the distal end 62 of the cylindrically shaped proximal section 58. In this embodiment the device has a second opening 44l which is an elongated longitudinally oriented slot. The second opening 44l a closed proximal end 78f and a closed distal end 80f. The closed distal end 80f of the second opening 44l is in the flared distal section 52 of the distal tubular portion 26. The closed proximal end 78f of the second opening 44l is in the cylindrically shaped proximal section 58. The third opening 70l has the same shape and orientation as the second opening 44l.

Additionally, the embodiment shown in FIGS. 15A and 15B includes a fourth opening 72d and a fifth opening 90. The fourth opening 72d is an elongated longitudinally oriented slot and has a closed proximal end 74d and a closed distal end 76d. The closed proximal end 74d of the fourth opening 72d is located at the proximal end 54 of the flared distal section 52. The closed distal end 76d of the fourth opening 72d is located in the flared distal section 52. The fourth opening 72d and the fifth opening 90 have lengths which are longer than the length of the second opening 44l and the third opening 70l.

FIGS. 16A and 16B show a distal tubular portion 26 of the tissue cutting member 16 which has a second opening 44m, a third opening 70m, a fourth opening 72e, and a fifth opening 90a. The second opening 44m is an elongated longitudinally oriented slot with a closed proximal 78g end and a closed distal end 80g. The closed proximal end 78g of the second opening 44m has an enlarged essentially circular shape 92 which is located at least partially in the distal end 62 of the cylindrically shaped proximal section 58. The closed distal end 80g of the second opening 44m is located in the flared distal section 52. The third opening 70m has the same shape and orientation as the second opening 44m. In this embodiment the closed proximal end 40 of the longitudinally oriented opening 36 is located at least partially in the distal end 62 of the cylindrically shaped proximal section 58.

The embodiment in FIGS. 16A and 16B also includes a fourth opening 72e and a fifth opening 90a. The fourth opening 72e is an elongated longitudinally oriented slot with a closed proximal end 74e and a closed distal end 76e. The closed proximal end 74e of the fourth opening 72e has an enlarged essentially circular shape 94 which is located at least partially in the distal end 62 of the cylindrically shaped proximal section 58. The closed distal end 76e of the fourth opening 72e is located in the flared distal section 52. The fourth opening 72e and the fifth opening 90a have a length which is longer than the length of the second opening 44m and the third opening 70m.

FIGS. 17A and 17B show a tubular distal portion 26 of the tissue cutting member 16 wherein the closed proximal end 40 of the longitudinally oriented opening 36 is located in the cylindrically shaped proximal section 58. This embodiment includes a second opening 44n and a third opening 70n. The second opening 44n is an elongated longitudinally oriented slot with a closed proximal end 78h and a closed distal end 80h. The closed proximal end 78h of the second opening 44n is located in the cylindrically shaped proximal section 58. The closed distal end 80h of the second opening 44n is located in the flared distal section 52. The third opening 70m has the same shape and orientation as the second opening 44n.

The embodiment in FIGS. 17A and 17B also has a fourth opening 72f and fifth opening 90b. The fourth opening 72f is an elongated longitudinally oriented slot with a closed proximal end 74f and a closed distal end 76f. The closed distal end 76f of the fourth opening 72f is located in the flared distal section 52. The closed proximal end 76f of the fourth opening 72f is located at the junction 64 between the flared distal section 52 and the cylindrically shaped proximal section 58. The fifth opening 90b has the same shape and orientation as the fourth opening 72f.

The embodiment of the device shown in FIGS. 18A and 18B has a second opening 44o which is an elongated longitudinally oriented slot with a closed distal end 80i and a closed proximal end 78i. The closed proximal end 78i of the second opening 44o has an enlarged essentially circular shape located in the cylindrically shaped proximal section 58. The closed distal end 80i of the second opening 44o is located in the flared distal section 52. The third opening 70o has the same shape and orientation as the second opening 44o.

The embodiment in FIGS. 18A and 18B also include a fourth opening 72g and a fifth opening 90c. The fourth opening 72g is an elongated longitudinally oriented slot with a closed proximal end 74g and a closed distal end 76g. The closed proximal end 74g of the fourth opening 72g is located at the proximal end 54 of the flared distal section 52. The closed distal end 76g of the fourth opening 72g is located in the flared distal section 52. The fifth opening 90c has the same shape and orientation as the fourth opening 72g. In this embodiment the closed proximal end 40 of the longitudinally oriented opening 36 is in the cylindrically shaped proximal section 54 of the distal tubular portion 26.

The tissue cutting members shown in 17A and 17B and 18A and 18B may have an additional opening 96 shown in phantom in FIG. 18A.

The tubular portion 28 of the tissue cutting member 16 is preferably formed of surgical grade stainless steel. However, other high strength materials such as MP35N, other cobalt-chromium alloys, NiTi alloys, ceramics, glasses, and high strength polymeric materials or combinations thereof may be suitable. Further details of the tissue cutting member 16 may be found in the above mentioned application Ser. No. 11/014,413, filed on Dec. 16, 2004.

While particular forms of the invention have been illustrated and described herein, it will be apparent that various modifications and improvements can be made to the invention. For example, while the various embodiments of the invention have been described herein in terms of a biopsy device, it should be apparent that the devices and methods of utilizing the device may be employed to remove tissue for purposes other than for biopsy, i.e. for treatment or other diagnoses. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such a "element", "member", "device", "section", "component", "portion", "section", "means", "step" and words of similar import, when used herein shall not be construed as invoking the provisions of 35 U.S.C. § 112(6) unless the following claims expressly use the terms "means" or "step" followed by a particular function without specific structure or action. All patents and patent applications referred to above are hereby incorporated by reference in their entirety.

What is claimed is:

1. A method for forming a tissue cutting member to separate a tissue specimen from a target site within a patient's body, comprising:
   providing a distal tubular portion including a side wall defining a lumen, a longitudinal axis, and a flared distal section;
   configuring the flared distal section to include an inclined distal tip at a distal end of the side wall and an outwardly flared distal tubular portion that defines an inner tissue receiving aperture, the inclined distal tip having a beveled front face with a leading cutting edge and a trailing cutting edge, the outwardly flared distal tubular portion being outwardly flared in a distal direction to the leading cutting edge;
   providing a single longitudinally oriented opening in the side wall in the flared distal section which radially opens to the lumen, the single longitudinally oriented opening having an open distal end and extending from a closed proximal end to the open distal end; and
   providing a relief opening at the closed proximal end, the relief opening having a transverse dimension larger than a transverse dimension of the single longitudinally oriented opening adjacent the relief opening, the single longitudinally oriented opening diverging from the closed proximal end to intersect the trailing cutting edge of the beveled front face of the inclined distal tip of the distal tubular portion and facilitating formation of the outwardly flared distal tubular portion.

2. The method of claim 1, wherein the relief opening has a substantially circular shape.

3. The method of claim 1, including providing the distal tubular portion with a cylindrically shaped proximal section, wherein the flared distal section extends in a distal direction from the cylindrically shaped proximal section.

4. The method of claim 3, including locating the relief opening at an intersection of the cylindrically shaped proximal section with the flared distal section of the distal tubular portion.

5. The method of claim 3, including locating the relief opening, in part, in each of the cylindrically shaped proximal section and the flared distal section of the distal tubular portion.

6. The method of claim 1, further comprising providing at least one annular slot located in the side wall in the flared distal section in a region between the relief opening and the inclined distal tip.

7. The method of claim 6, wherein the at least one annular slot includes two diametrically opposed annular slots.

8. The method of claim 1, including providing at least one circular opening located in the side wall in the flared distal section in a region between the relief opening and the inclined distal tip.

9. The method of claim 8, wherein the at least one circular opening includes two diametrically opposed circular openings.

10. The method of claim 1, including providing the distal tubular portion with a cylindrically shaped proximal section, the flared distal section extending in a distal direction from the cylindrically shaped proximal section, and locating at least one annular slot at an intersection of the cylindrically shaped proximal section with the flared distal section of the distal tubular portion.

11. The method of claim 10, wherein the at least one annular slot includes two diametrically opposed annular slots.

12. The method of claim 1, including providing the distal tubular portion with a cylindrically shaped proximal section, the flared distal section extending in a distal direction from the cylindrically shaped proximal section, and locating at least one circular opening at an intersection of the cylindrically shaped proximal section with the flared distal section of the distal tubular portion.

13. The method of claim 12, wherein the at least one circular opening includes two diametrically opposed circular openings.

14. A method for forming a biopsy probe, comprising:
providing an elongated outer cannula having a side wall, a distal tip, and a first tissue receiving aperture located in the side wall of the elongated outer cannula that is spaced proximally from the distal tip; and
providing a tissue cutting member slidably disposed within the elongated outer cannula, including:
providing the tissue cutting member with a distal tubular portion including a side wall defining a lumen, a longitudinal axis, and a flared distal section, the flared distal section having an inclined distal tip at a distal end of the side wall and an outwardly flared distal tubular portion that defines an inner tissue receiving aperture, the inclined distal tip having a beveled front face with a leading cutting edge and a trailing cutting edge, the outwardly flared distal tubular portion being outwardly flared in a distal direction to the leading cutting edge; and
providing a single longitudinally oriented opening in the side wall in the flared distal section which radially opens to the lumen, the single longitudinally oriented opening having an open distal end and extending from a closed proximal end to the open distal end, the closed proximal end having a relief opening with a transverse dimension larger than a transverse dimension of the single longitudinally oriented opening adjacent the relief opening, the single longitudinally oriented opening diverging from the closed proximal end to intersect the trailing cutting edge of the beveled front face of the inclined distal tip of the distal tubular portion and facilitating formation of the outwardly flared distal tubular portion.

15. The method of claim 14, wherein the relief opening has a substantially circular shape.

16. The method of claim 14, including providing the distal tubular portion with a cylindrically shaped proximal section, the flared distal section extending in a distal direction from the cylindrically shaped proximal section.

17. The method of claim 16, including locating the relief opening at an intersection of the cylindrically shaped proximal section with the flared distal section of the distal tubular portion.

18. The method of claim 14, including locating at least one annular slot in the side wall in the flared distal section in a region between the relief opening and the inclined distal tip.

19. The method of claim 14, including locating at least one circular opening in the side wall in the flared distal section in a region between the relief opening and the inclined distal tip.

\* \* \* \* \*